United States Patent
Somes et al.

(10) Patent No.: US 11,268,957 B2
(45) Date of Patent: Mar. 8, 2022

(54) SUBSTRATE READER AND METHOD OF READING A SUBSTRATE

(71) Applicant: GenPrime, Spokane, WA (US)

(72) Inventors: Jason Buck Somes, Spokane, WA (US); Darby Dawn McLean, Spokane Valley, WA (US); Michael Arthur Russell, Spokane, WA (US)

(73) Assignee: GenPrime, Spokane, WA (US)

( * ) Notice: Subject to any disclaimer, the term of this patent is extended or adjusted under 35 U.S.C. 154(b) by 341 days.

(21) Appl. No.: 16/432,673

(22) Filed: Jun. 5, 2019

(65) Prior Publication Data
US 2020/0386753 A1    Dec. 10, 2020

(51) Int. Cl.
*G01N 33/558* (2006.01)
*G01N 35/00* (2006.01)
*G01N 21/77* (2006.01)

(52) U.S. Cl.
CPC ..... *G01N 33/558* (2013.01); *G01N 35/00029* (2013.01); *G01N 2021/7786* (2013.01); *G01N 2035/00108* (2013.01)

(58) Field of Classification Search
CPC .......... G01N 2021/7786; G01N 2035/00108; G01N 21/8483; G01N 27/3273; G01N 33/558; G01N 35/00029; G01N 35/00732
See application file for complete search history.

(56) References Cited

U.S. PATENT DOCUMENTS

| | | | |
|---|---|---|---|
| 2009/0155921 A1* | 6/2009 | Lu .................. | G01N 21/274 436/164 |
| 2013/0183772 A1* | 7/2013 | Fleming ............ | G01N 21/8483 436/501 |
| 2015/0111201 A1 | 4/2015 | Ozcan et al. | |
| 2015/0310634 A1* | 10/2015 | Babcock .................. | G06T 7/90 382/165 |
| 2016/0202190 A1* | 7/2016 | Hein .................. | G01N 21/8483 422/69 |

OTHER PUBLICATIONS

PCT Search Report and Written Opinion dated Jul. 27, 2020 for PCT Application No. PCT/US20/30530, 9 pages.

* cited by examiner

*Primary Examiner* — Jennifer Wecker
*Assistant Examiner* — Jonathan Bortoli
(74) *Attorney, Agent, or Firm* — Lee & Hayes, P.C.

(57) ABSTRACT

A device including a light source, one or more actuators, and an image capturing device. The device is operable to receive a request to capture image data of a sample, determine at least one of an analyte being tested within the sample or a container holding the sample, position the image capturing device relative to the sample based on the analyte being tested or the container holding the sample, illuminate the light source based on the analyte being tested or the container holding the sample, capture the image data, and send the image data to one or more computing devices for image processing.

20 Claims, 12 Drawing Sheets

SUBSTRATE READER AND METHOD OF READING A SUBSTRATE

BACKGROUND

Numerous methods and systems have been developed for conducting chemical, biochemical, and/or biological testing. These methods and systems are essential in a variety of applications including medical diagnostics, food and beverage testing, environmental monitoring, manufacturing quality control, and drug discovery. For example, lateral flow assays or assay test strips, are membranes designed to detect the presence (or absence) of an analyte. In assay test strips, a fluid sample is placed at or near one end of the membrane and is carried to an opposite end by capillary action. The analyte, if present, reacts with a reagent in the membrane to produce a visual indication. Visual inspection, however, is prone to interpretation errors and fails to provide quantitative measurement. Additionally, assay test strips often require the expertise of trained technicians in laboratory settings and using sophisticated, expensive, and bulky instruments. Laboratory testing also increases the cost of analysis and may delay results.

In an effort to overcome these deficiencies, automated and semi-automated assay test strip readers have been developed. Some of these devices, however, may require interpretation by a user. Furthermore, existing devices are often configured or designed for a particular test, assay test strip, cartridge holding the assay test strip, and/or analyte being tested. For example, certain devices may be limited to receiving certain types of assay test strips or cartridges. As a result, existing devices are not capable of universal assay test strip reading.

BRIEF DESCRIPTION OF THE DRAWINGS

The detailed description is set forth below with reference to the accompanying figures. In the figures, the left-most digit(s) of a reference number identifies the figure in which the reference number first appears. The use of the same reference number in different figures indicates similar or identical items. The systems depicted in the accompanying figures are not to scale and components within the figures may be depicted not to scale with each other.

DETAILED DESCRIPTION

Figure 1:
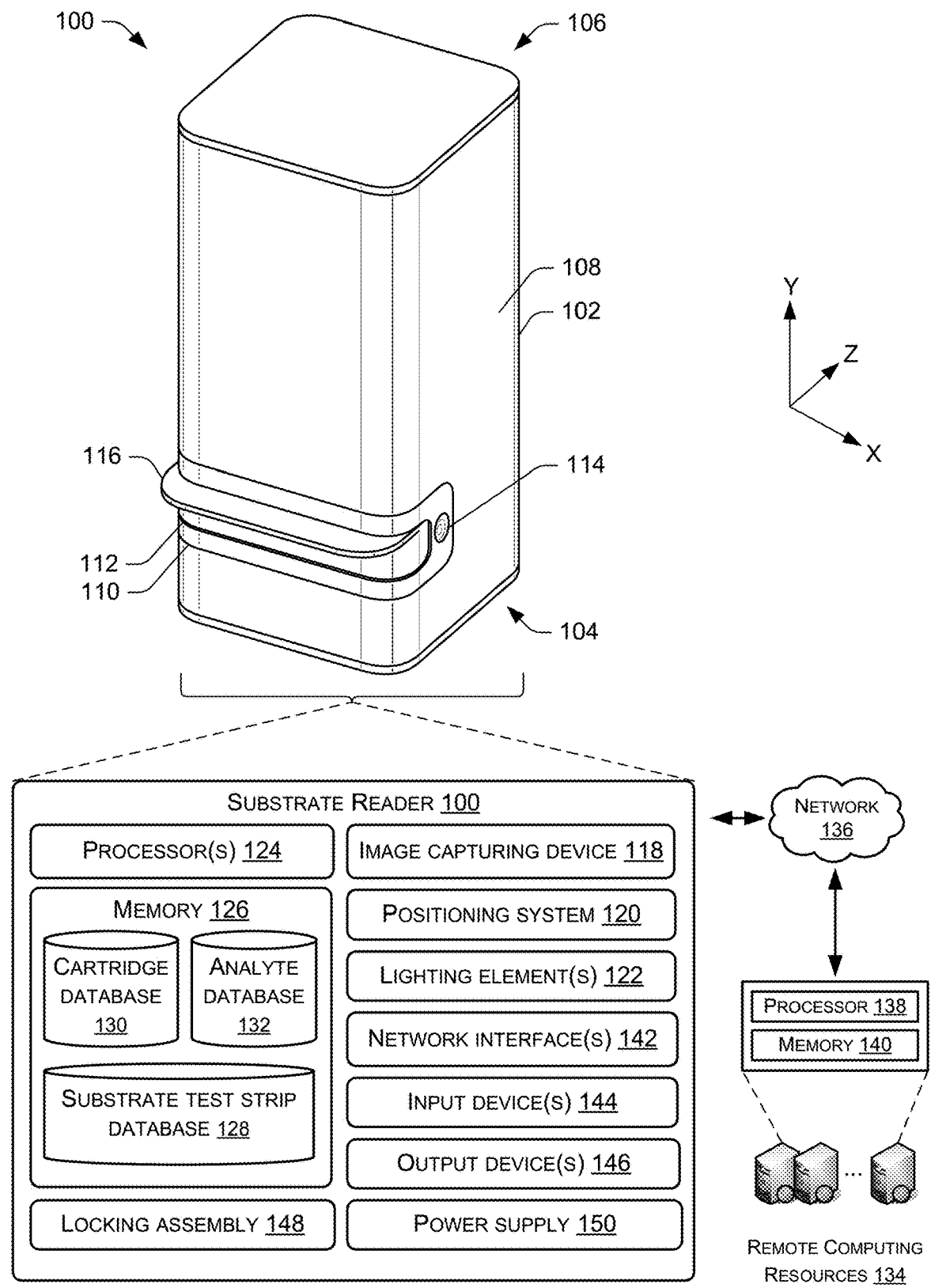
FIG. 1 is a perspective view of an example substrate reader and shows example computing components of the substrate reader, according to an embodiment of the present disclosure.

Systems and methods are currently available for conducting chemical, biochemical, and/or biological testing. However, currently available methods require visual inspection, are prone to interpretation errors, and do not provide quantitative measurements. While the introduction of automated and semi-automated devices has reduced human error, or the amount of training required by laboratory technicians, conventional devices are limited to performing tests on certain substrate test strips, certain substrate test strip cartridges, or certain analytes. Existing devices may also fail to align imaging equipment relative to the substrate test strip and/or properly illuminate regions of interest on the substrate test strip. As a result, conventional devices are often inefficient, may have low sensitivity to detect certain analytes, and/or may lack universal use across a multitude of applications. Accordingly, there exists a need for a device that may accurately read or capture images of a substrate test strip for use in determining the presence and/or concentration of analytes contained in a fluid sample.

This disclosure describes a substrate reader with improved image capturing and reading capabilities. The substrate reader is designed and configured to image a substrate test strip (e.g., lateral flow assay test strip, assay test strip, etc.) for use in detecting or measuring the presence of an analyte(s) contained in a fluid sample (e.g., blood, urine, mucus, serum, saliva, plasma, etc.). The substrate reader may capture images of the substrate test strip, or a portion thereof, and using the captured images, the substrate reader and/another communicatively coupled computing device may analyze the images to provide qualitative, semi-quantitative, and/or quantitative results. Such automation may reduce subjectivity, visual interpretation, training required by technicians, and/or other sources of human-perceived error. Additionally, the substrate reader may be customizably configured depending on the substrate test strip, the substrate test strip cartridge, and/or the analyte being tested.

The substrate reader may include a housing having components configured to receive, position, and image the substrate test strip. For example, in an embodiment, the housing may include a drawer, canister, port, or slide configured to receive the substrate test strip. In an embodiment, the substrate test strip is contained within a cartridge that holds the substrate test strip. In an embodiment, the substrate reader may receive a plurality of cartridges and/or different types of cartridges, such as cups (e.g., smart cup with embedded test strip), container, cassettes, dip cards, etc. for holding various fluids, samples, or substrate test strips. For example, as cartridges include different shapes, sizes, and geometries, the slide may include pins, fins, protrusions, flanges, shelves, or other receptacles configured to receive and hold various types of cartridges, containers, or samples.

In an embodiment, the slide may include features that position and align the cartridge and/or the substrate test strip relative to one or more components within the housing. For example, the features may align the substrate test strip and/or the cartridge relative to an image capturing device configured to image and/or read the substrate test strip. In such embodiments, the slide may also include features that mate with corresponding features of the cartridge to hold and align the cartridge with the image capturing device.

The slide may operably transition between an open state and a closed state. In the open state, the slide may receive the substrate test strip and/or the cartridge. For example, an operator may place the substrate test strip and/or the cartridge in the slide and may move the slide between the open and closed state. In the closed state, the substrate reader may capture images of the substrate test strip and/or analyze the images to determine a presence (or lack thereof) of an analyte. In an embodiment, in the closed state, and while the substrate reader is imaging or otherwise reading the substrate test strip, the slide may lock. However, upon imaging the substrate test strip or after analyzing the substrate test strip, the slide may unlock to permit removal or replacement (e.g., exchanging) of substrate test strips.

In an embodiment, the slide may couple to motors, biasing members, or other actuators that operably open and close the slide. For example, the slide may open and close with a press of a button disposed on the housing of the substrate reader. In an embodiment, springs or other mechanisms may control a rate at which the slide opens and closes to prevent fluids within the cartridge from spilling.

Within the housing, the image capturing device may capture, sense, or otherwise read the substrate test strip. For example, the image capturing device may include a camera, photodetector, photoresistor, high-resolution flatbed scanner, or other sensors to capture images of the substrate test strip. In an embodiment, the image capturing device may image or read a region of interest, or a particular portion, of the substrate test strip, such as a region indicating a presence of the analyte, a concentration level, etc. As the presence of the analyte is evidenced by a visually detectable coloring region of the substrate test strip, the image capturing device may capture images for analysis. In other words, the image capturing device may obtain light intensity measurements of the substrate test strip and the substrate reader and/or a communicatively coupled computing device may analyze the one or more images. For example, the substrate reader and/or the communicatively coupled computing device may compare depth values, light intensity measures, and/or color values to a database to determine the presence (or absence) of the analyte within the fluid sample. In an embodiment, based on the analysis and/or the comparison, the substrate reader and/or the communicatively coupled computing device may provide qualitative, semi-quantitative, and/or quantitative results.

The substrate reader may include one or more lighting elements to emit light onto the substrate test strip while the image capturing device captures images. For example, the lighting elements may include light emitting diodes (LEDs) or organic light emitting diodes (OLEDs) that direct, focus, or emit light onto the substrate test strip or a particular region on the substrate test strip. In an embodiment, the lighting elements may be broadband or narrowband, may be polarized or non-polarized, and/or may emit different colors of light. In an embodiment, the lighting elements may encircle, surround, or be disposed around the substrate test strip. Moreover, in an embodiment, the substrate reader may include a light diffuser to uniformly disperse light onto the substrate test strip.

The substrate reader may adjust, accommodate, or be configured according to the substrate test strip (e.g., lateral flow) and/or the cartridge (e.g., single well or multi-well assay cartridges). Additionally, or alternatively, the substrate reader may be configured according to the analyte being tested. That is, as noted above, as substrate test strips and cartridges are of varying shapes, size, and compositions, the image capturing device may reposition to capture accurate and/or improved images of the substrate test strip. Additionally, or alternatively, the brightness of light emitted on the substrate test strip may affect a quality of images captured. Failing to configure the substrate reader according to the substrate test strip, the cartridge, and/or the analyte being tested, may affect the imaging or quality of images captured, which in turn may impact accuracy or sensitivity in detecting the analyte.

In an embodiment, the substrate reader may include mechanisms, such as motors and actuators, that align the image capturing relative to the substrate test strip and/or the cartridge to accommodate for various substrate test strips, cartridges, and/or analytes being tested. For example, the image capturing device may be disposed on a track or positioning system, or may couple to motors, drives, or other actuators that align the image capturing device relative to the substrate test strip (or a portion thereof). In an embodiment, the actuators may maneuver the image capturing device in horizontal and/or vertical directions relative to the substrate test strip. In an embodiment, the actuators may also tilt or dispose the image capturing device at certain angles relative to the substrate test strip. As noted above, aligning the image capturing device may increase image quality of captured images.

Additionally, or alternatively, the lighting elements may adjust to accommodate for various substrate test strips, cartridges, and/or analytes being tested. For example, a brightness (lux) or color of light emitted by the lighting elements may change based on the cartridge. Controlling a brightness of the lighting element, a color of the lighting elements, and/or focusing the lighting element to illuminate a particular region of interest of the substrate test strip (e.g., the detection region) may reduce an amount of noise within captured images. For example, materials or features of the cartridge may reflect light emitted by the lighting elements, which may introduce noise into the captured image. Reducing an amount of noise in the captured images (e.g., bright spots) may increase a sensitivity of the substrate reader and/or reduce the incidence of erroneous results for low concentrations of analytes. Additionally, or alternatively, substrate test strips may produce different visual indications (e.g., color, location, etc.) depending on specifics of the substrate test strip and the analyte being tested.

In an embodiment, the substrate reader may determine the type and characteristics of the substrate test strip, the cartridge, and/or analyte(s) being tested via an identifier (e.g., barcode, quick response code (GR code), a series of numbers, data matrix, etc.) disposed on the test sample. For example, the substrate reader may capture an image of the identifier, analyze the image, and determine specific characteristics and associated imaging needs particular to the substrate test strip, the cartridge, and/or the analyte being tested. Using this information, the image capturing device and/or the lighting elements may adjust, reposition, or reconfigure. In an embodiment, the image capturing device may capture an image of the identifier. Additionally, or alternatively, the substrate reader may include additional sensors (e.g., scanner) configured to capture, or otherwise read, the identifier. Regardless of the type of identifier or sensor to read identifier, the information obtained analyzing the identifier may be utilized by the substrate reader to position the image capturing device and/or adjust the brightness of the lighting elements.

In light of the above, the substrate reader may be configured according to and/or adjust to accommodate a range of testing. For example, the substrate reader may be utilized to detect a wide range of analytes, including but not limited to hormones, vitamins, glucose proteins, peptides, steroids, bacteria, fungi, viruses, parasites, allergens, antigens, drugs, metabolites, antibodies, microorganisms, malignant cells, etc. Such tailoring to the test sample by the substrate reader may provide greater accuracy and/or reduce the need for separate and/or exclusive customized readers. As such, the substrate reader disclosed herein may find uses within many industries including healthcare, waste-disposal, military, food science, homeland security, and/or fermentation science, and/or may be used by government agencies, police and fire departments, municipalities, hospitals, laboratories or other workplace testing sites, ethanol production facilities, collection sites, wineries, and/or breweries. The substrate reader may therefore function as a universal reader to detect a range of analytes used across a divergent range of disciplines.

While the instant disclosure is described in use with substrate test strips, such as qualitative or semi-quantitative lateral flow assay test strips, the substrate reader and the techniques and methods described herein are not limited to such embodiments. For example, the techniques and methods described herein may find use with other imaging analysis platforms and/or may analyze other sample test strips (e.g., microspot array tests, non-lateral flow assays tests, cups with embedded test strips, etc.), liquids, gases, solids, compositions of matter, etc.

The present disclosure provides an overall understanding of the principles of the structure, function, device, and system disclosed herein. One or more examples of the present disclosure are illustrated in the accompanying drawings. Those of ordinary skill in the art will understand that the devices and/or the systems specifically described herein and illustrated in the accompanying drawings are non-limiting embodiments. The features illustrated or described in connection with one embodiment may be combined with the features of other embodiments, including as between systems and methods. Such modifications and variations are intended to be included within the scope of the appended claims.

FIG. 1 illustrates a perspective view of a substrate reader 100 designed and configured to analyze or otherwise read substrate test strips (e.g., lateral flow test strip). The substrate reader 100 includes a housing 102 that provides a protective enclosure for components of the substrate reader 100 and which may carry out a function of the substrate reader 100. In an embodiment, the substrate reader 100 may be designed and sized to reside on countertops, shelves, desks, and/or tables within homes, medical facilities, laboratories, etc. Additionally, the substrate reader 100 may be lightweight and transportable between different locations. As discussed in detail herein, within the housing 102, the substrate reader 100 may capture images of substrate test strip(s) for use in determining the presence (or absence) of an analyte contained within a fluid sample.

The housing 102 may include a base 104, a top 106, and an exterior surface 108 that extends between the base 104 and the top 106. As shown, the housing 102 may have an elongated square shape extending between the base 104 and the top 106. However, the housing 102 may include tubular shapes, rectangular shapes, circular shapes, triangular shapes, hexagonal shapes, etc. As shown, the exterior surface 108 may include chamfered and rounded edges. Additionally, the housing 102 may include a variety of materials, including plastics, composites, metals, and/or a combination thereof.

In an embodiment, the substrate reader 100 may include a cabinet 110 that removably attaches or couples to the housing 102, and a slide 112 that removably attaches or couples to the cabinet 110. To receive the cabinet 110, the housing 102 includes an opening disposed through the exterior surface 108 and/or a sidewall of the housing 102. The cabinet 110 may removably couple to housing 102 to accommodate for various substrate test strips and/or samples being tested. For example, the cabinet 110 (and the slide 112) may be removed to permit the housing 102 to receive different containers.

To permit an operator to grasp the cabinet 110 to disengage the cabinet 110 from the housing 102 and/or engage the cabinet 110 with the housing 102, the cabinet 110 may include depressions, indents, or other structural features 114. In an embodiment, the housing 102 and/or the cabinet 110 may include corresponding flanges, ribs, slots, or other interacting structural features that align and engage with one another to position the cabinet 110 with the housing 102. For example, the housing 102 and the cabinet 110 may include alignment elements that allow the cabinet 110 to glide or otherwise transition into and out of the housing 102.

The slide 112 is insertable within cabinet 110. The slide 112 may receive the substrate test strip or cartridge, and is configured to transition between an open state and a closed state. FIG. 1 illustrates the slide 112 in the closed close, whereby the substrate reader 100 may image and read the substrate test strip. Comparatively, in the open state, an operator may remove the substrate test strip or the cartridge and insert a new substrate test strip (or cartridge).

In an embodiment, the slide 112 may include a handle 116 that allows the operator to grip or otherwise grasp the slide 112 to assist in transitioning the slide 112 between open and closed states. In an embodiment, the cabinet 110 and/or the slide 112 may include corresponding flanges, ribs, slots, or other interactive structural features that align and engage with one another to position the slide 112 with the housing 102 and/or the cabinet 110. For example, the cabinet 110 and the slide 112 may include corresponding alignment tabs that allow the slide 112 to move in and out within the cabinet 110.

The slide 112 may receive a wide variety of different types of substrate test strips or cartridges. For example, and as will be discussed in detail herein, the slide 112 may include ports or other receptacles for receiving the cartridge and/or which align the cartridge within the slide 112.

As noted above, the substrate reader 100 is configured to image substrate test strips within an interior of the housing 102. For example, the substrate reader 100 may include an image capturing device 118 to capture images of the substrate test strip(s). In an embodiment, the slide 112 may align the substrate test strip (or the cartridge) with the image capturing device 118. Additionally, or alternatively, the substrate reader 100 may include a positioning system 120 that aligns the image capturing device 118 with the substrate test strip. For example, as the slide 112 may receive a wide variety of different types of substrate test strips or cartridges, the positioning system 120 may align the image capturing device 118 with the substrate test strip. The positioning system 120 may also align the image capturing device 118 with, or relative to, a specific area, zone, or region of the substrate test strip, such as a detection region that indicates the presence (or absence) of the analyte being tested.

In an embodiment, the positioning system 120 may maneuver the image capturing device 118 in horizontal and/or vertical directions relative to the substrate test strip (e.g., X-, Y-, and/or Z-directions). In an embodiment, the positioning system 120 may also tilt or dispose the image capturing device 118 at certain angles relative to the substrate test strip. For example, the positioning system 120 may include mounts, brackets, gears, slides, tracks, motors, wheels, pulleys, pneumatics, hydraulic cylinders, cables, screw drives, turntables, or other actuators that position, move, or orient the image capturing device 118. In an embodiment, the positioning system 120 may be manually controlled by an operator of the substrate reader 100. For example, the operator may actuate (e.g., push, pull, rotate, twist, etc.) one or more dials, levers, or knobs of the positioning system 120 to position the image capturing device 118. Additionally, or alternatively, components of the positioning system 120 may be electric or motorized and controlled by logic or other hardware of the substrate reader 100, according to aspects of the specific substrate test or cartridge being tested.

The substrate reader 100 may include lighting element(s) 122 that emit light onto the substrate test strip to illuminate the substrate test strip for image capturing by the image capturing device 118. For example, within the housing 102, the lighting element(s) 122 may surround, encircle, or be disposed around, above, or to a side of the substrate test strip. In an embodiment, a brightness of the lighting element(s) 122 may adjust depending on the substrate test strip, the cartridge, and/or the analyte being tested. Additionally, or alternatively, the lighting element(s) 122 may output various colors, polarizations, and/or wavelengths based on the substrate test strip, the cartridge, and/or the analyte. For example, in an embodiment, the lighting element(s) 122 may comprise white light LEDs or may include colored LEDs.

In some examples, the substrate reader 100 may include multiple lighting element(s) 122 or multiple printed circuit boards (PCBs) including the lighting element(s) 122 disposed thereon for illuminating the substrate test strip, the cartridge, and/or the image capturing device 118. For example, a first lighting element may illuminate the substrate test strip and a second lighting element may provide light for the image capturing device 118.

To determine characteristics of substrate test strip, the cartridge, and/or the analyte being tested, the substrate reader 100 may read an identifier of the substrate test strip and/or the cartridge. For example, the cartridge may include a barcode. That is, to determine the characteristics of the substrate test strip, the cartridge, and/or the analyte being tested for purposes of adjusting the lighting and/or positioning the image capturing device 118, the substrate reader 100 may image the barcode and determine information pertinent or related to testing the substrate test strip. As an example, the information may include or identify the substrate test strip, the cartridge, the analyte being tested, the patient (e.g., age, sex, medical history, etc.), etc. Using this information, the substrate reader 100 may adapt, be configured, and/or adjust one or more components of the substrate reader 100, such as positioning of the image capturing device 118, via the positioning system 120, and/or adjusting the brightness of the lighting element(s) 122.

As illustrated, the substrate reader 100 may include processor(s) 124 and memory 126, which stores or otherwise has access to a substrate test strip database 128, a cartridge database 130, and/or an analyte database 132. Upon capturing or sensing the identifier, the processor(s) 124 may compare the identifier against the substrate test strip database 128, the cartridge database 130, and/or the analyte database 132. Such comparison may function to identify the substrate test strip, the cartridge, and/or the analyte being tested. For example, the substrate test strip database 128, the cartridge database 130, and/or the analyte database 132 may store an indication or information associated with a positioning of the image capturing device 118, an amount of brightness to illuminate the substrate test strip via the lighting element(s) 122, and/or a color of light to emit on the substrate test strip via the lighting element(s) 122.

To align the image capturing device 118 with the substrate test strip, or a portion thereof, the processor(s) 124 may transmit a control signal to the positioning system 120. Additionally, or alternatively, the processor(s) 124 may transmit a control signal to the lighting element(s) 122 to adjust in brightness and/or color. Accordingly, after the substrate reader 100 configures according to the substrate test strip, the cartridge, and/or the analyte being tested, the image capturing device 118 may capture image data of the substrate test strip. For example, the image capturing device 118 may image the detection region and capture image data for analysis.

In an embodiment, the processor(s) 124 may determine a wet-up period, a wait period, or a time to capture image(s). For example, as a fluid sample is placed on the substrate test strip, or within a sample receiving zone of the cartridge, the substrate reader 100 may delay or wait until capturing images of the substrate test strip to allow the fluid sample to flow (by capillary action) from the sample receiving zone to the test region. The rate at which the fluid flows, or an amount of time before the analyte is capable of being detected (if present), may depend on the substrate test strip, the cartridge, and/or the analyte. Accordingly, after identifying the characteristics, the processor(s) 124 may determine a delay or predetermined amount of time before the image capturing device 118 captures images. However, in an embodiment, kinetic analysis may be used to determine the early detection, or presence, of the analyte such that the image capturing device 118 may not wait for the entire wet-up period before imaging the substrate test strip.

In an embodiment, the substrate reader 100 may operate in conjunction with or may otherwise utilize remote computing resources 134. For example, the substrate reader 100 may communicatively couple to the remote computing resources 134 over a network 136. The remote computing resources 134 may be implemented as one or more servers and may, in an embodiment, form a portion of a network-accessible computing platform implemented as a computing infrastructure of processors, storage, software, data access, etc. that is maintained and accessible via a network such as the Internet. The remote computing resources 134 do not require end-user knowledge of the physical location and configuration of the system that delivers the services. Common expressions associated for these remote computing devices 134 include "on-demand computing", "software as a service (SaaS)", "platform computing", "network-accessible platform", "cloud services", "data centers", etc.

The substrate reader 100 may communicatively couple to the network 136 via wired technologies (e.g., wires, USB, fiber optic cable, etc.), or may include network interface(s) 142 (e.g., RF, cellular, satellite, Bluetooth, etc.), or other connection technologies for communicating with the network 136. The network 136 is representative of any type of communication network, including data and/or voice network, and may be implemented using wired infrastructure (e.g., cable, CAT5, fiber optic cable, etc.), a wireless infrastructure (e.g., RF, cellular, microwave, satellite, Bluetooth, etc.), and/or other connection technologies.

The remote computing resources 134 include a processor 138 and memory 140, which may store or otherwise have access to some or all of the components described with reference to the memory 126 of the substrate reader 100. For example, the memory 140 may have access to and utilize the substrate test strip database 128, the cartridge database 130, and/or the analyte database 132 for identifying and/or determining characteristics of the substrate test strips, the cartridges, and/or analytes being assayed, respectively.

In some examples, the substrate reader 100 may upload image data captured by the image capturing device 118 to the remote computing resources 134 for processing, given that the remote computing resources 134 may have a computational capacity that far exceeds the computational capacity of the substrate reader 100. The substrate reader 100 may therefore utilize the remote computing resources 134 for performing relatively complex analysis on the image data captured. For example, the remote computing resources 134 may compare the image data received from the substrate reader 100 against a database of historical data, results learned from previous images captured, and/or may utilize one or more machine-learning algorithms to identify the presence (or absence) of an analyte. In an embodiment, the remote computing resources 134 may perform image processing on the image data to provide qualitative, semi-quantitative, and/or quantitative results. In an embodiment, the results may be transmitted back to the substrate reader 100, to one or more third-party databases, or to other electronic devices (e.g., mobile phone, tablet, computers, etc.). Regardless of whether the image processing occurs locally on the substrate reader 100 or remote from the substrate reader 100, images captured by the image capturing device 118 may be used to determine the presence (or absence) of the analyte within the fluid sample.

Upon completion the image processing, the substrate reader 100 may output one or more visual indications indicating a completion. For example, the substrate reader 100 may receive an indication from the remote computing resources 134 indicating that the remote computing resources 134 have successfully identified the analyte or lack thereof. In an embodiment, if the remote computing resources 134 (or the substrate reader 100) are unable to perform image processing, the remote computing resources 134 may transmit a request to the substrate reader 100 to capture one or more additional images. For example, the images captured may have poor image quality and the request may cause the image capturing device 118 to capture additional images for uploading to the remote computing resources 134. In some examples, in receiving the request from the remote computing resources 134, the processor(s) 124 may adjust a position of the image capturing device 118 and/or a lighting characteristic of the lighting element(s) 122.

In an embodiment, the substrate reader 100 may include various input device(s) 144 and/or various output device(s) 146. In an embodiment, the input device(s) 144 may include buttons, touch screens, switches, joystick, trackballs, mouse, etc. for receiving input. For example, the input device(s) 144 may include a touch screen in which the operator inputs details or information relating to the substrate test strip, the cartridge, the analyte being tested, a positioning of the image capturing device 118, and/or settings of the lighting element(s) 122. In an embodiment, the output device(s) 146 may include loudspeakers, light indicators, touch screens, display screens, haptic actuators, etc. for outputting an operational state or other indications to the operator. For example, the output device(s) 146 may include a display screen that displays results of the image processing indicating the presence and/or concentration of the analyte. As another example, the output device(s) 146 may include a light indicator that emits red light during a testing of the substrate test strip and emit a green light upon a completion of the image processing. Additionally, or alternatively, the substrate test strip may output an audible indication via one or more loudspeakers.

In an embodiment, the substrate reader 100 may include a locking assembly 148. In an embodiment, in the closed state, and while the substrate reader 100 is imaging or otherwise reading the substrate test strip, the locking assembly 148 may lock the cabinet 110 and/or the slide 112 to prohibit opening of the cabinet 110 and/or the slide 112. Upon imaging the substrate test strip, or after analyzing the substrate test strip, the locking assembly 148 may unlock the cabinet 110 and/or the slide 112 to permit removal or replacement (e.g., exchanging) of substrate test strips.

A power supply 150 supplies power to components of the substrate reader 100, such as the processor(s) 124, the image capturing device 118, and/or the lighting element(s) 122. In an embodiment, the power supply 150 may include a replaceable battery or a rechargeable battery. In other embodiments, the substrate reader 100 may be powered by mains power or by an external host device (e.g., a computer connected by a USB cable).

Although the substrate reader 100 is illustrated with certain components, the substrate reader 100 may include additional hardware, logic, modules, and/or other components.

As used herein, a processor, such as processor(s) 124 and/or 138 may include multiple processors and/or a processor having multiple cores. Further, the processor(s) may comprise one or more cores of different types. For example, the processor(s) may include application processor units, graphic processing units, etc. In one implementation, the processor(s) may comprise a microcontroller and/or a microprocessor. The processor(s) may include a graphics processing unit (GPU), a microprocessor, a digital signal processor or other processing units or components known in the art. Alternatively, or in addition, the functionality described herein can be performed, at least in part, by one or more hardware logic components. For example, and without limitation, illustrative types of hardware logic components that may be used include field-programmable gate arrays (FPGAs), application-specific integrated circuits (ASICs), application-specific standard products (ASSPs), system-on-a-chip systems (SOCs), complex programmable logic devices (CPLDs), etc. Additionally, each of the processor(s) may possess its own local memory, which also may store program components, program data, and/or one or more operating systems.

The memory 126 and/or 140 may include volatile and nonvolatile memory, removable and non-removable media implemented in any method or technology for storage of information, such as computer-readable instructions, data structures, program component, or other data. Such memory may include, but is not limited to, RAM, ROM, EEPROM, flash memory or other memory technology, CD-ROM, digital versatile disks ("DVD") or other optical storage, magnetic cassettes, magnetic tape, magnetic disk storage or other magnetic storage devices, RAID storage systems, or any other medium which can be used to store the desired information and which can be accessed by a computing device. The memory may be implemented as computer-readable storage media ("CRSM"), which may be any available physical media accessible by the processor(s) to execute instructions stored on the memory. In one basic implementation, CRSM may include random access memory ("RAM") and Flash memory. In other implementations, CRSM may include, but is not limited to, read-only memory ("ROM"), electrically erasable programmable read-only memory ("EEPROM"), or any other tangible medium which can be used to store the desired information and which can be accessed by the processor(s).

Figure 2:
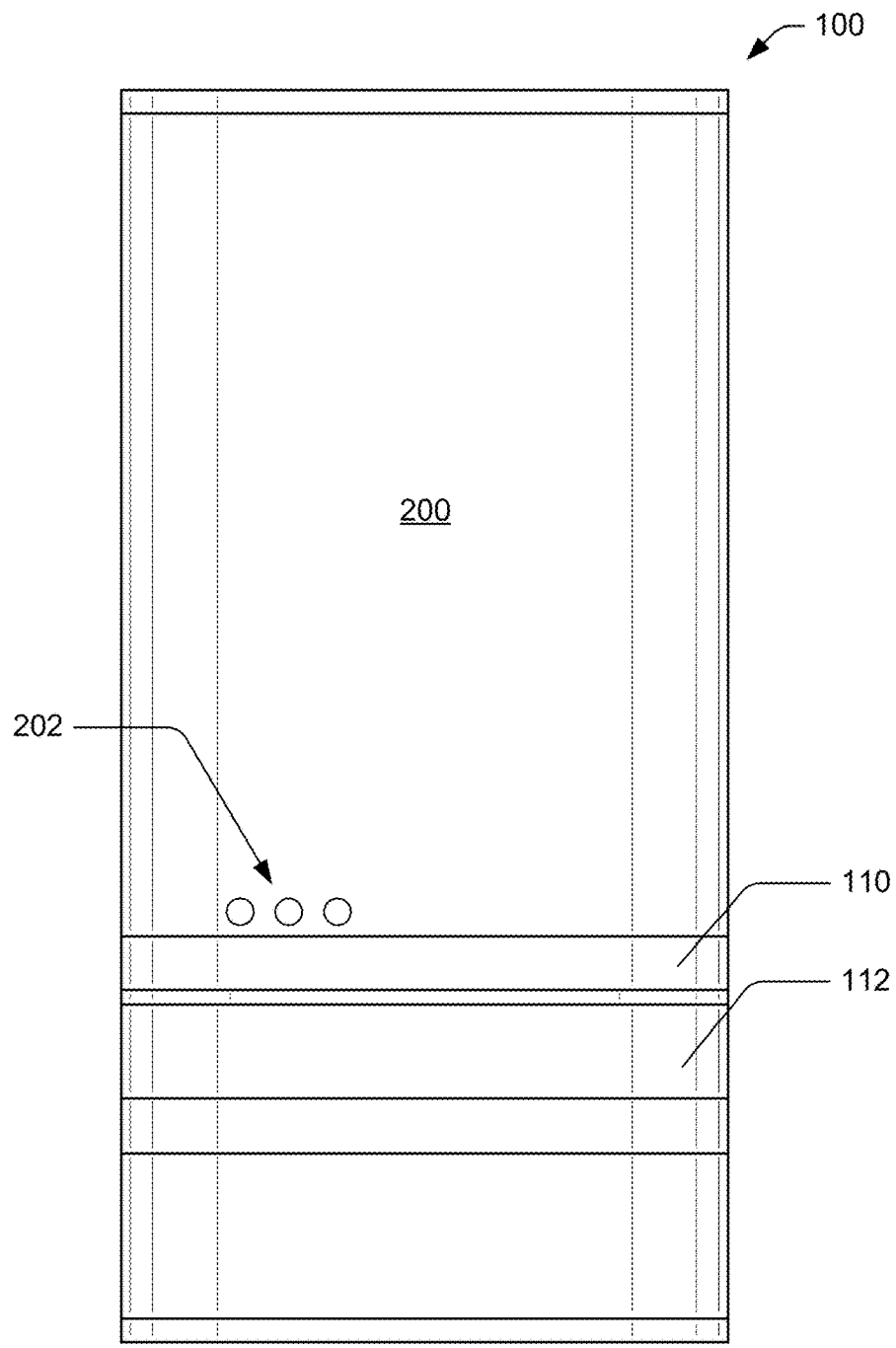
FIG. 2 is a first side view of the substrate reader of FIG. 1, according to an embodiment of the present disclosure.

FIG. 2 illustrates a first side 200 of the substrate reader 100. In an embodiment, the first side 200 may correspond to a front of the substrate reader 100. As such, the cabinet 110 and/or the slide 112 may be located on the front of the substrate reader 100.

In an embodiment, the first side 200 may include a light indicator 202. For example, as shown in FIG. 2, the light indicator 202 may include a series of three lights, which in an embodiment, may illuminate to different colors or states (e.g., flashing). In an embodiment, the light indicator 202 may indicate an operational state of the substrate reader 100. As an example, a first light of the light indicator 202 may illuminate red to indicate the substrate reader 100 is capturing an image of the substrate test strip, a second light of the light indicator 202 may illuminate yellow to indicate the substrate reader 100 and/or the remote computing resources 134 are performing image analysis, and a third light of the light indicator 202 may illuminate green to indicate testing is complete. However, in other embodiments, the light indicator 202 may utilize a single light to indicate operational states of the substrate reader 100. Further, the light indicator 202 may be disposed on additional or other sides of the housing 102, or may be oriented in different manners on the housing 102 (e.g., ring).

Figure 3:
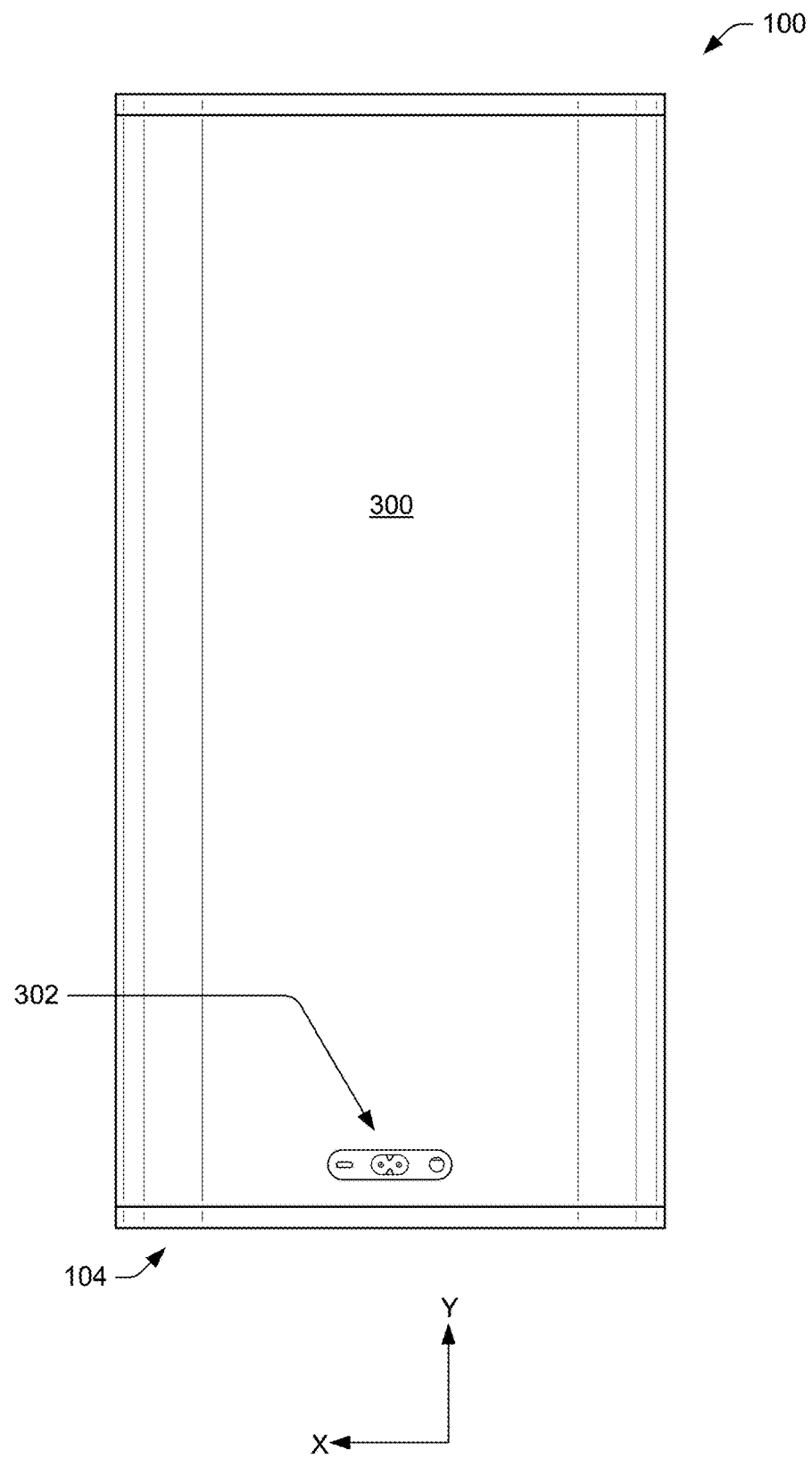
FIG. 3 is a second side view of the substrate reader of FIG. 1, according to an embodiment of the present disclosure.

FIG. 3 illustrates a second side 300 of the substrate reader 100. In an embodiment, the second side 300 of the substrate reader 100 may correspond to a back of the substrate reader 100. In this sense, the second side 300 may be opposite (Z-direction) the first side 200 of the substrate reader 100. The second side 300 may include ports 302. As shown in FIG. 3, the ports 302 may be located proximate to the base 104 of the housing 102. In an embodiment, the ports 302 may comprise a power port for powering the substrate reader 100, audio jacks, and/or a USB port. However, the substrate reader 100 may additionally, or alternatively, include other input/output ports. Moreover, in an embodiment, the substrate reader 100 may include a rechargeable battery for cordless operation.

Figure 4:
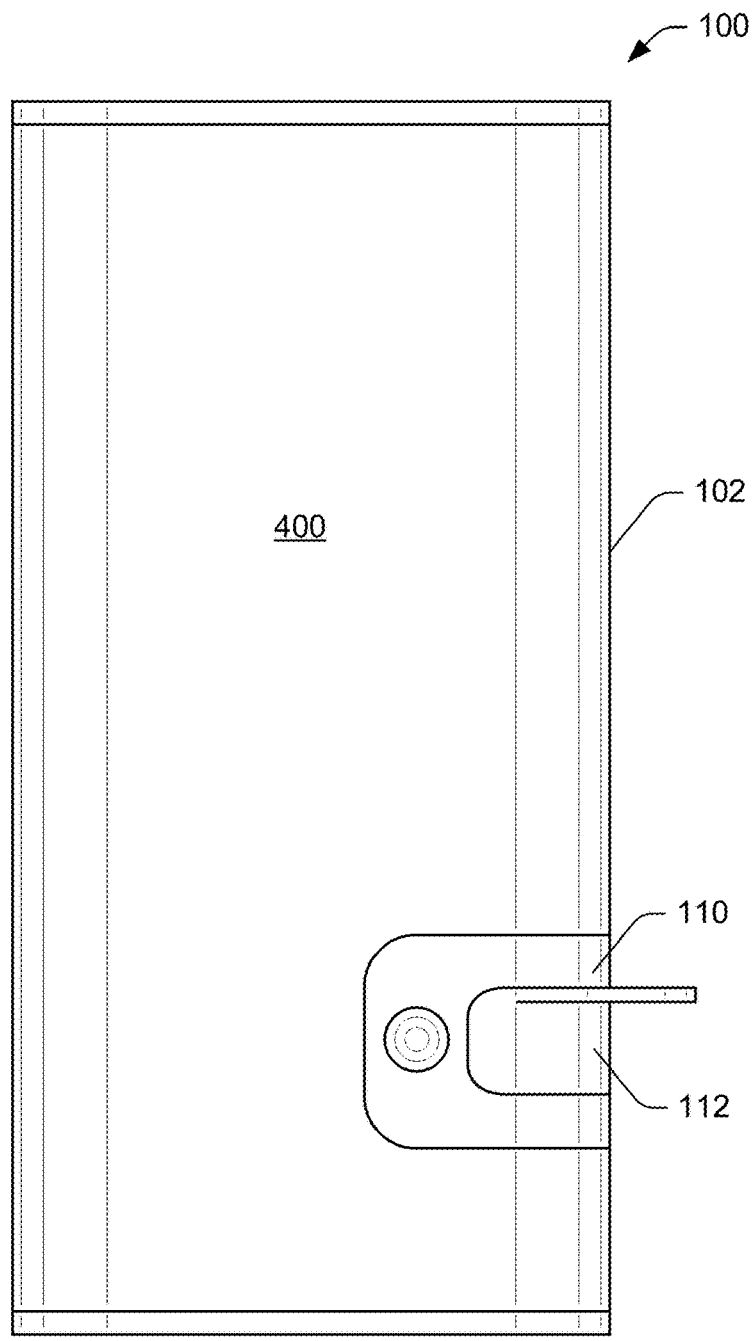
FIG. 4 is a third side view of the substrate reader of FIG. 1, according to an embodiment of the present disclosure.

FIG. 4 illustrates a third side 400 of the substrate reader 100, which may correspond to a first lateral side of the substrate reader 100. As shown in FIG. 4, when the cabinet 110 and the slide 112 couple to the housing 102, portions (e.g., sides) of the cabinet 110 and the slide 112 may be disposed along or at the third side 400. Accordingly, an opening of the housing 102 to receive the cabinet 110 may at least partially extend through the third side 400.

Figure 5:
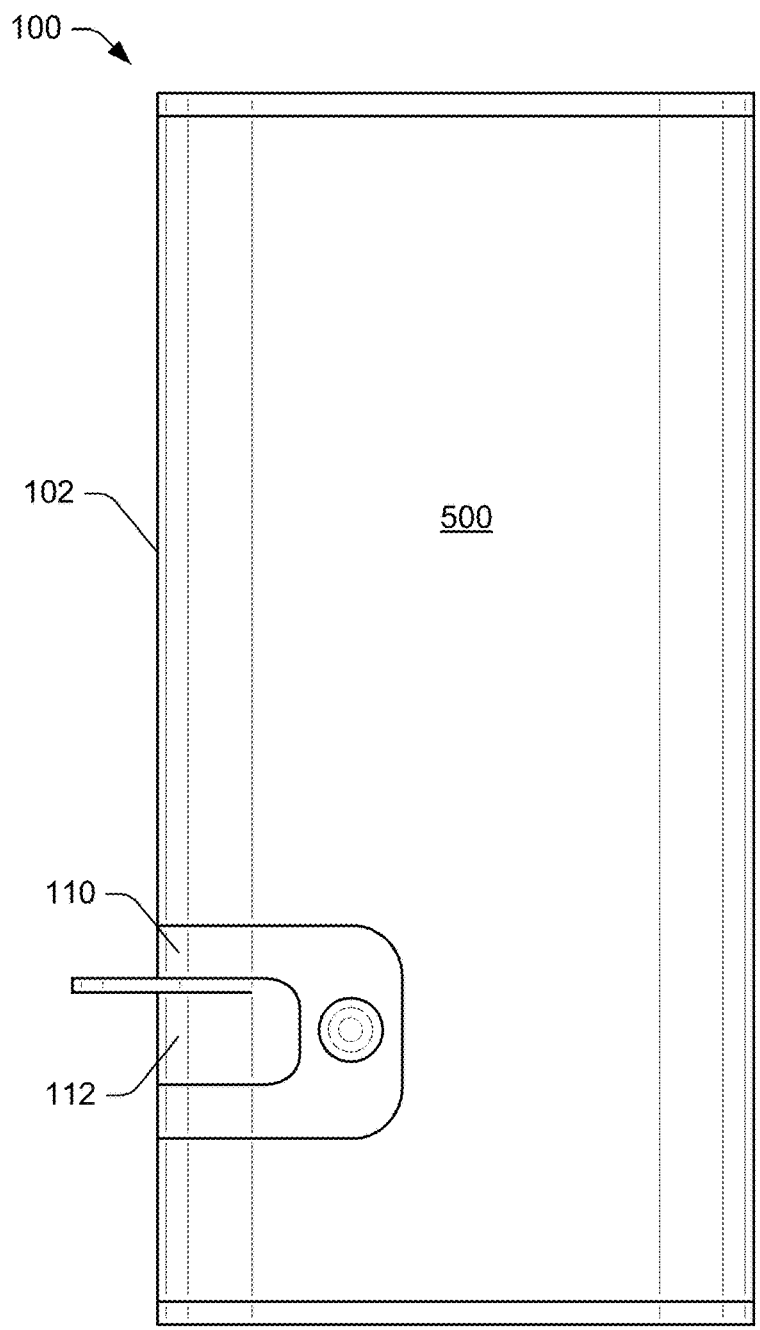
FIG. 5 is a fourth side view of the substrate reader of FIG. 1, according to an embodiment of the present disclosure.
Figure 5:
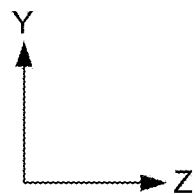

FIG. 5 illustrates a fourth side 500 of the substrate reader 100, which may correspond to a second lateral side of the substrate reader 100, opposite the third side 400 (X-direction). As shown in FIG. 5, when the cabinet 110 and the slide 112 couple to the housing 102, portions (e.g., sides) of the cabinet 110 and the slide 112 may be disposed along or at the fourth side 500. Accordingly, in an embodiment, the opening of the housing 102 to receive the cabinet 110 may extend through the first side 200, the third side 400, and/or the fourth side 500.

Figure 6:
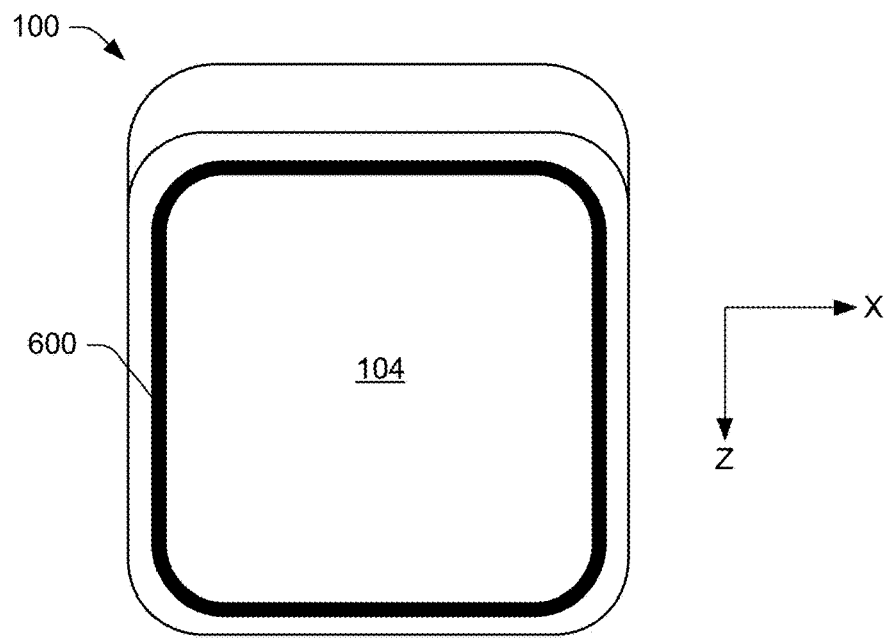
FIG. 6 is a top view of the substrate reader of FIG. 1, according to an embodiment of the present disclosure.

FIG. 6 illustrates the base 104 of the substrate reader 100. The base 104 may assist in enclosing an interior of the substrate reader 100. In an embodiment, the base 104 may include a pad 600 (e.g., rubber, foam, etc.) that secures the substrate reader 100 within an environment, such as on a desk, counter, shelf, etc.

Figure 7:
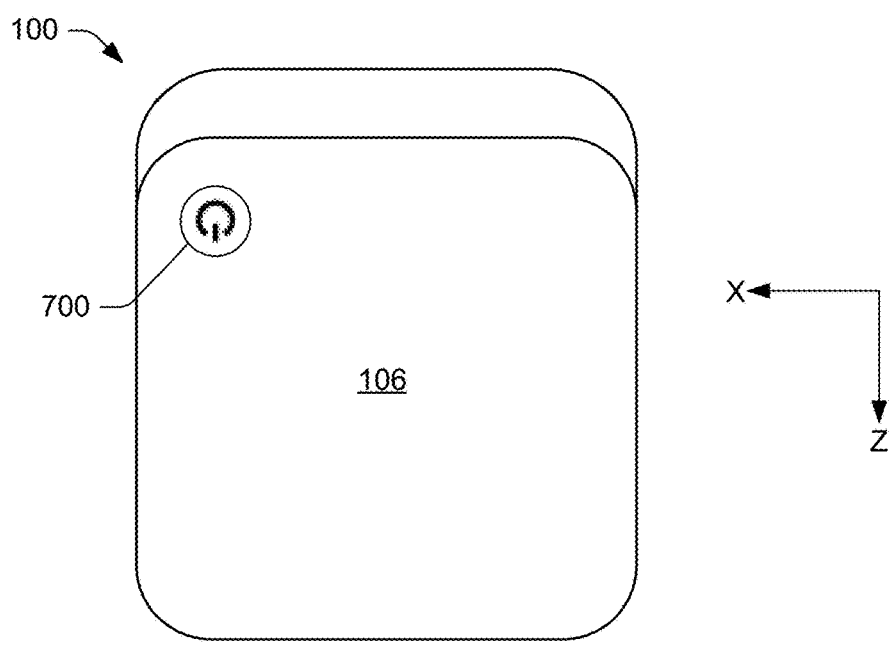
FIG. 7 is a bottom view of the substrate reader of FIG. 1, according to an embodiment of the present disclosure.

FIG. 7 illustrates the top 106 of the substrate reader 100. The top 106 may assist in enclosing an interior of the substrate reader 100. In an embodiment, the top 106 may include a button 700 for powering on and off the substrate reader 100. Additionally, or alternatively, the button 700 may be located elsewhere, such as on the first side 200, the second side 300, the third side 400, and/or the fourth side 500. Additionally, or alternatively, the button 700 may include different functionalities (e.g., pairing, mute, test, etc.).

Figure 8:
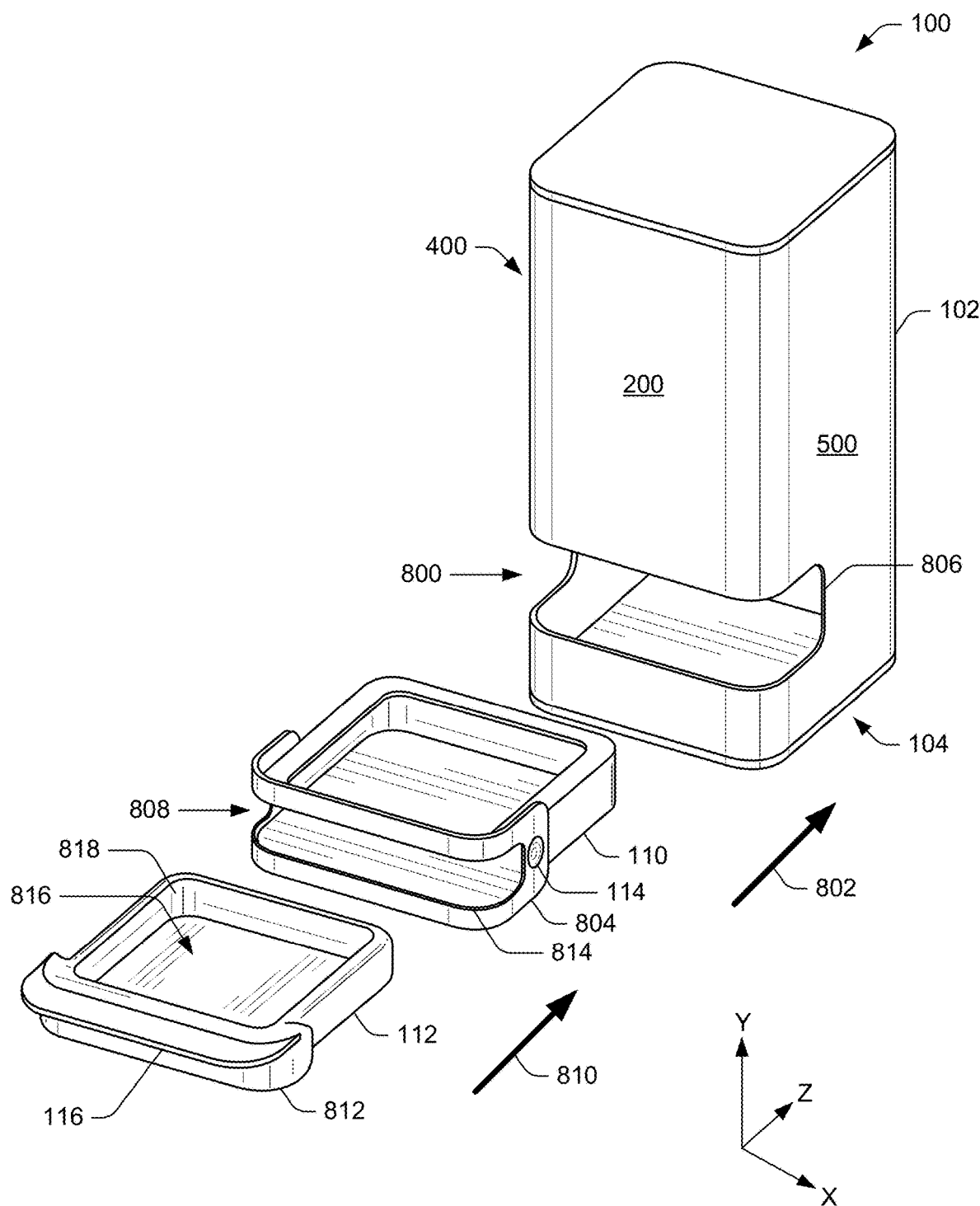
FIG. 8 is a partial exploded view of the substrate reader of FIG. 1, showing a slide and a cabinet disposed from a housing of the substrate reader, according to an embodiment of the present disclosure.

FIG. 8 illustrates a partially exploded view of the substrate reader 100. More particularly, FIG. 8 illustrates the cabinet 110 and the slide 112 disposed away from the housing 102. As shown in FIG. 8, the housing 102 includes an opening 800 within which the cabinet 110 may reside when coupled to the housing 102. For example, the cabinet 110 may insert into the opening 800 in a direction as indicated by the arrow 802. In an embodiment, the opening 800 may be disposed through the first side 200, the third side 400, and/or the fourth side 500. Although shown being disposed proximate to the base 104, in an embodiment, the opening 800 may be located proximate to the top 106 and/or may be disposed through other sides of the housing 102. Moreover, the opening 800 may include alternative shapes than shown.

The cabinet 110 is sized and configured to insert within the opening 800 and engage with the housing 102. For example, the cabinet 110 may include a flange 804 that engages with a lip, border, or annulus 806 of the opening 800. When inserted, an exterior surface of the flange 804 may align or substantially align (e.g., co-planar) with the exterior surface 108 along the first side 200, the third side 400, and/or the fourth side 500, respectively. As mentioned above, the features 114 on the cabinet 110 may assign in removing and inserting the cabinet 110 into and out of the opening 800 (and the housing 102).

The cabinet 110 includes an opening 808 for receiving the slide 112. In an embodiment, the slide 112 may insert into the opening 808 after the cabinet 110 couples to the housing 102 or before the cabinet 110 couples to the housing 102 (i.e., the cabinet 110 and the slide 112 may couple to the housing 102 as a single unit). The slide 112 may insert into the opening 808 in a direction as indicated by arrow 810.

In an embodiment, the slide 112 may include a flange 812 that engages with a lip, border, or annulus 814 of the opening 808. When inserted, an exterior surface of the flange 812 may align or substantially align (e.g., co-planar) with the flange 804 of the cabinet 110 and/or the exterior surface 108 along the first side 200, the third side 400, and/or the fourth side 500, respectively. As mentioned above, the slide 112 may include the handle 116 to assist in removing and inserting the slide 112 into and out of the opening 808.

The slide 112 includes a receptacle 816 for receiving substrate test strips and/or cartridges. The receptacle 816 may represent an area in which the substrate test strip(s)

and/or the cartridges are placed. In this sense, the receptacle 816 may correspond to a container, enclosure, bin, hopper, receptacle, or other area for receiving the substrate test strips and/or cartridges. However, in an embodiment, the receptacle 816 may receive items other than substrate test strip(s) and/or cartridges. For example, the receptacle 816 may receive liquids, solids, or other compositions. Additionally, or alternatively, the receptacle 816 may receive cups, canisters, or other holders having embedded test strips.

In an embodiment, the slide 112 may include sidewalls 818 for containing the substrate test strip(s) and/or the cartridges within the receptacle 816. In an embodiment, the slide 112 may prevent samples or other fluids from spilling into an interior of the housing 102.

As will be discussed herein with regard to FIG. 9, in an embodiment, the slide 112 may include features designed and configured to position cartridges. Notably, as cartridges may include different shapes, sizes, designs, and geometries, the receptacle 816 may include features (e.g., pins, protrusions, flanges, shelves, etc.) that hold, align, and/or position the cartridge. For example, multi-well cartridges may take a variety of forms, sizes and shapes. Such positioning, in an embodiment, may align the cartridge and/or the substrate test strip relative to one or more components within the housing 102, such as the image capturing device 118.

The cabinet 110, the slide 112, and/or other components of the housing 102 may include gaskets or seals that prevent or substantially prevent ambient light entering the housing 102. The seals may block ambient light from negatively effecting captured images, which may increase a sensitivity or accuracy when detecting analytes contained within a fluid sample. Additionally, components of the housing 102, such as the cabinet 110 and/or the slide 112, may be manufactured from materials having low reflectance. Such materials may assist in reducing glare or bright spots within captured images.

Figure 9:
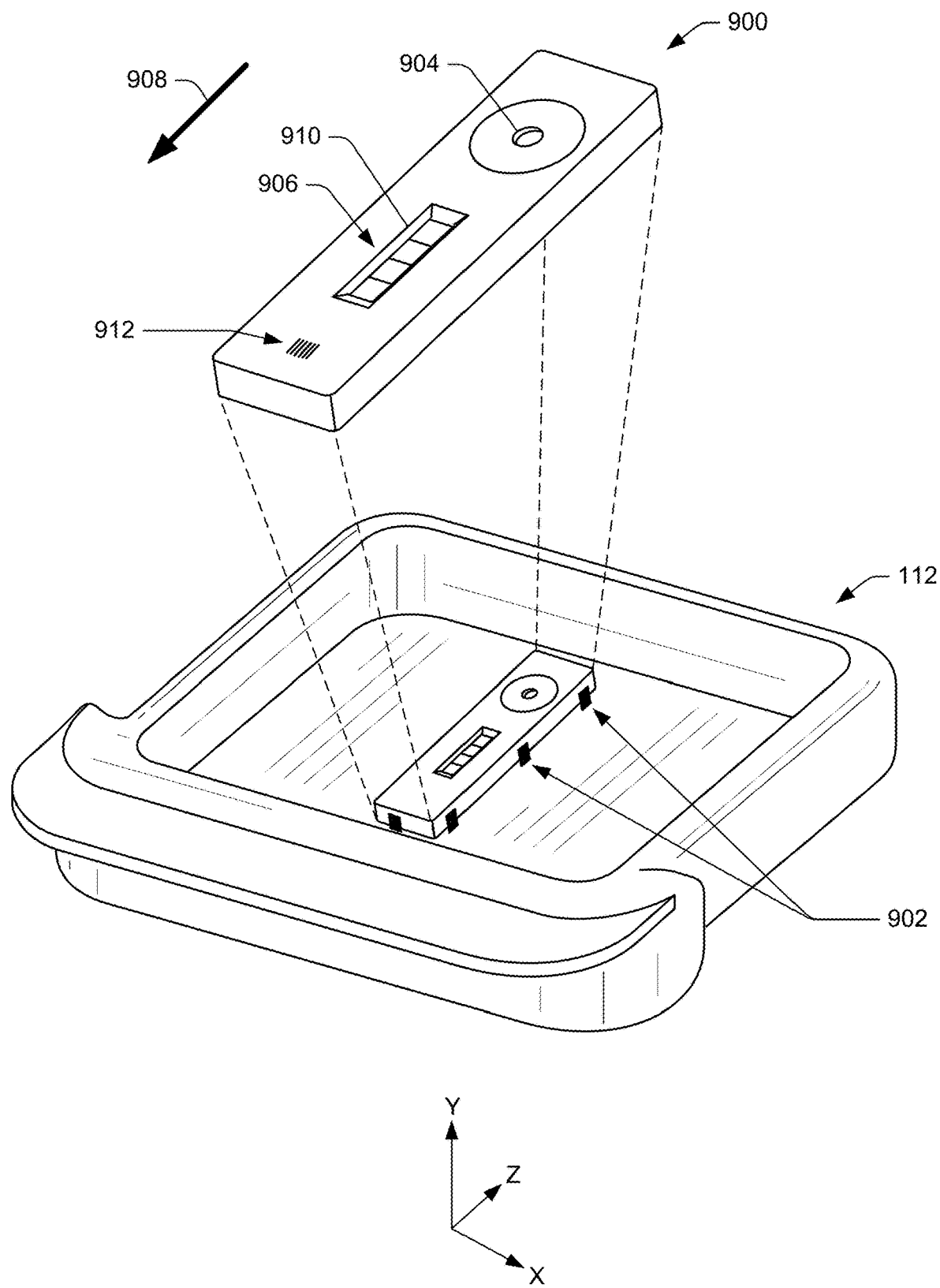
FIG. 9 illustrates an example cartridge disposed within the slide of FIG. 8, according to an embodiment of the present disclosure.

FIG. 9 illustrates an example cartridge 900 disposed with the slide 112. The cartridge 900 may contain a substrate test strip. As discussed above, the slide 112 may include includes receptacle(s) 902 configured to hold the cartridge 900. In an embodiment, the receptacle(s) 902 may clutch or engage with multiple sides of the cartridge 900, such as lateral sides, a top, a bottom, etc. Additionally, or alternatively, the receptacle(s) 902 may engage with corners, depressions, or other extrusions on the cartridge 900. In an embodiment, the receptacle(s) 902 may center the cartridge 900 within the slide 112 and/or relative to the image capturing device 118.

The cartridge 900 includes a sample receiving region 904 to receive a fluid sample. As shown, the sample receiving region 904 may represent a trough, well, or funnel to direct the fluid sample onto the substrate test strip contained within the cartridge 900. The substrate test strip includes a flow path for the fluid sample and a reagent that specifically binds a target analyte within a test region 906. As such, the substrate test strip is made of a material that allows the fluid sample to flow from the sample receiving region 904 to the test region 906 by capillary action. Upon application of the fluid sample within the sample receiving region 904, the sample flows in the direction indicated by arrows 908.

In an embodiment, depending on characteristics of the fluid sample and/or the substrate test strip, there may be a wet-up phase. During the wet-up phase, and prior to being detectable, the substrate test strip may experience a visible change as the fluid sample moves along the length of the substrate test strip in a direction indicated by the arrow 908. After the wet-up phase, the analyte may become detectable at the test region 906. However, in an embodiment, kinetic analysis may be used for early identification or detection of the analyte.

The test region 906 is exposed for optical inspection via an opening 910 in the cartridge 900. In other words, the opening 910 exposes the test region 906 of the substrate test strip for visual inspection or imaging by the image capturing device 118.

While FIG. 9 illustrates a particular cartridge (e.g., single well), as discussed above, the slide 112 may receive a plurality of different types (e.g., size, shape, multi-well, etc.) and the image capturing device 118 may be configured according to the substrate test strip, the cartridge, and/or the analyte being tested. To accommodate for different cartridges, the slide 112 may include features to receive and position the substrate test strip. Additionally, or alternatively, the features may include locating mechanisms, springs, alignment tabs, etc. for positioning cartridge(s). In an embodiment, the slide 112 may include features that sequentially receive multiple cartridge types.

The cartridge 900 may include an identifier 912, such as a barcode, for identifying the substrate test strip, the cartridge 900, and/or the analyte being tested. Although illustrated as a barcode, the cartridge 900 may include other identifiers such as QR codes, a series of numbers, etc. The image capturing device 118 of the substrate reader 100, or another sensor, may capture an image of the identifier 912. The processor(s) 124 of the substrate reader 100 may analyze the identifier 912, in relation to the cartridge database 130, to identify the analyte being tested, the patient, the type of cartridge, the type of substrate test strip (e.g., a location of the test region 906) for enabling the image capturing device 118 to capture images. For example, in an embodiment, the substrate reader 100 may utilize the information contained in the identifier 912 to align the image capturing device 118 relative to the substrate test strip (or cartridge 900) and/or may configure the lighting element(s) 122 to output a certain brightness, sequence of lights, color of lights, etc.

Figure 10:
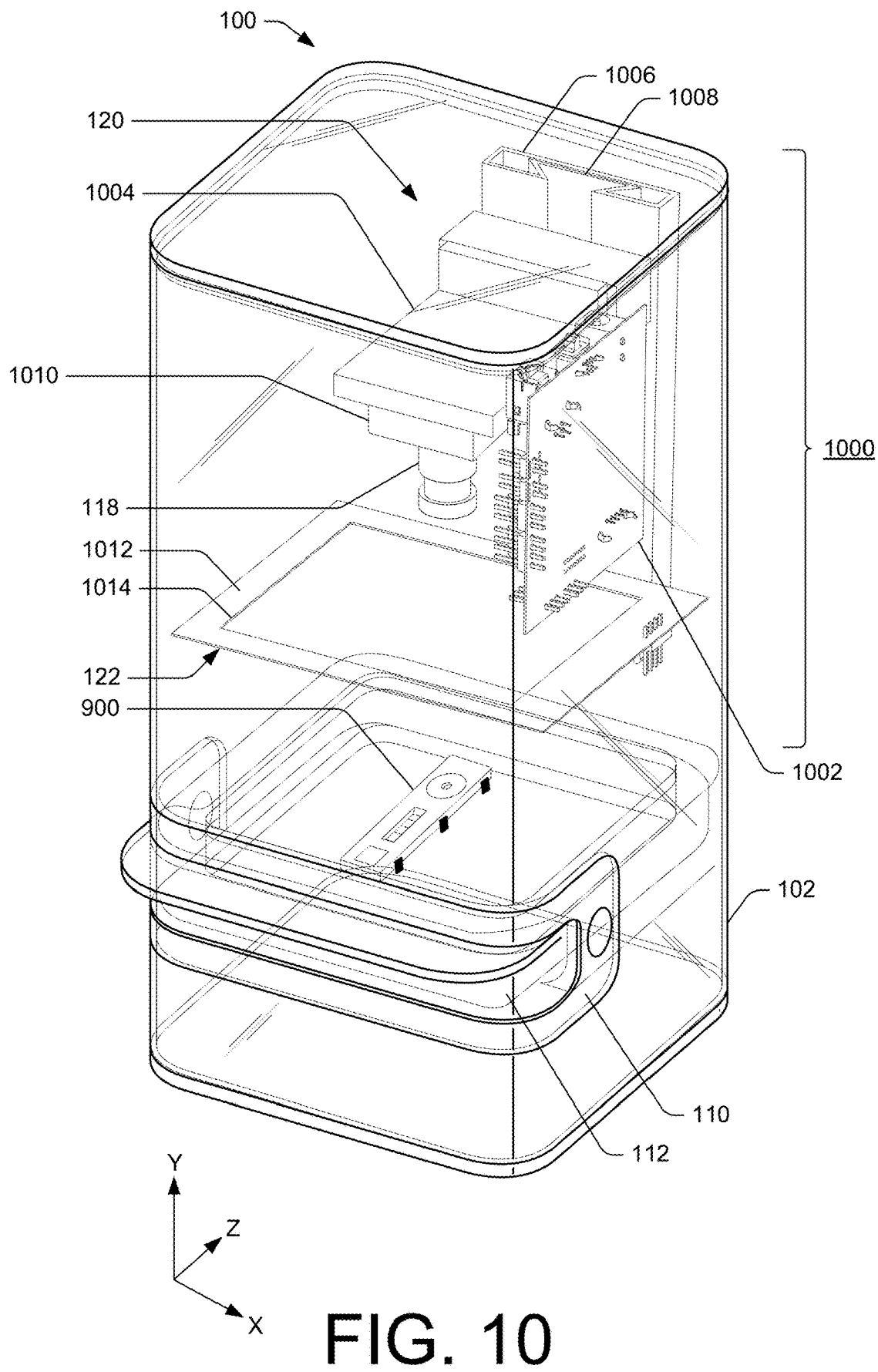
FIG. 10 is a perspective view of the substrate reader of FIG. 1, showing example components housed within the substrate reader, according to an embodiment of the present disclosure.

FIG. 10 illustrates example components of the substrate reader 100 disposed within the housing 102. The housing 102 is shown as transparent to illustrate the example components of the substrate reader 100. In an embodiment, the example components may be disposed within a top portion 1000 of the substrate reader 100, disposed vertically above (Y-direction) the cabinet 110, the slide 112, and the cartridge 900.

In an embodiment, the example computing components include the image capturing device 118 for optical inspection of exposed areas of the substrate test strip (e.g., the test region 906), the positioning system 120, the lighting element(s) 122 for emitting light onto the substrate test strip, and/or a PCB 1002. As shown, the image capturing device 118 may be oriented to capture images (e.g., image data) of the substrate test strip and/or the cartridge 900 for analysis. As shown, the image capturing device 118 is oriented towards the base 104 of the substrate reader 100, or towards the cabinet 110 and/or the slide 112 (Y-direction). In an embodiment, the image capturing device 118 may be centered within the housing 102 (X- and Z-directions) and configured to translate in the Y-direction. For example, the image capturing device 118 may couple to the positioning system 120 to translate, move, or reposition within the housing 102.

In an embodiment, the positioning system 120 may include mounts 1004 operably coupled to a track 1006. The mounts 1004 may couple within a slot 1008 of the track 1006. The image capturing device 118 may vertically translate (Y-direction) in the track 1006 through the mounts 1004 disengaging and engaging with the slot 1008. For example, fasteners may secure the mounts 1004 to the track 1006 and within the slot 1008. Loosening the fasteners may permit the mounts 1004 to move along a length of the track 1006 (Y-direction), thereby repositioning the image capturing device 118 within the housing 102 and relative to the substrate test strip. However, the positioning system 120 may additionally, or alternatively include swings, booms, arms to permit movement of the image capturing device 118.

In an embodiment, the positioning of the image capturing device 118 within the housing 102 may be controlled by motors, pneumatics, electromechanical devices, piezo electrics, turntables, stepper-motors, screw drives, or other actuators. In an embodiment, the image capturing device 118 may couple to the mount 1004 via a carrier 1010. The carrier 1010 may represent a multi-axis positioning system having linear positioning actuators that translate the image capturing device 118 in multiple axes (e.g., X-, Y-axis, and Z-axis). The carrier 1010 may therefore allow for precise orientation of the image capturing device 118 along multiple axes. Upon receiving an indication regarding the substrate test strip, the cartridge 900, and/or the analyte being tested, for example, the positioning system 120 may automatically, or manually via operator input, be used to position the image capturing device 118. The positioning system 120 may also include components that adjust an angle at which the image capturing device 118 is disposed relative to the assay test cartridge. In this sense, the positioning system may have six degrees of freedom including translational (X-direction, Y-direction, Z-direction) and angular translation (pitch, roll, and yaw).

The lighting element(s) 122 is shown disposed on a square-shaped PCB 1012 that encircles or surrounds the cartridge 900. The image capturing device 118 may be oriented to capture images through an opening 1014 of the PCB 1012 on which the lighting element(s) 122 are disposed. In an embodiment, the lighting element(s) 122 may include a plurality of LEDs (or other lighting sources) configured to direct and shine light on the substrate test strip. As such, the LEDs may be disposed around the cartridge and illuminate the substrate test strip for obtaining one or more images.

The PCB 1002 may include hardware and components to carry out functions of the substrate reader 100, such as processors, memory, circuits, transformers, power supplies, network interfaces (e.g., Wi-Fi, Bluetooth, ZigBee, Bluetooth Low Energy (BLE)), thermal pads, loudspeakers, antennas, etc. However, although certain components have been illustrated and described, the PCB 1002 and/or the substrate reader 100 may include additional components.

As discussed above, while the image capturing device 118 is imaging the substrate test strip, the substrate reader 100 may lock the cabinet 110 and/or slide 112 via the locking assembly 148. Upon completion of the imaging, the locking assembly 148 may unlock to permit the cabinet 110 and/or slide 112 to be removed.

Additionally, although the substrate reader 100 is illustrated as testing a fluid sample in an upright position (e.g., standing on the base 104), in an embodiment the substrate reader 100 may be configured to test fluid samples at other orientations. For example, the substrate reader 100 may rest on the second side 300 (e.g., the back of the substrate reader 100). In an embodiment, the cabinet 110 and the slide 112 may be removed from the housing 102 such that the fluid sample may be placed into the opening 800. Therein, the image capturing device 118 may capture and image of the fluid sample and/or the lighting element(s) 122 may adjust according to a lighting configuration.

Figure 11:
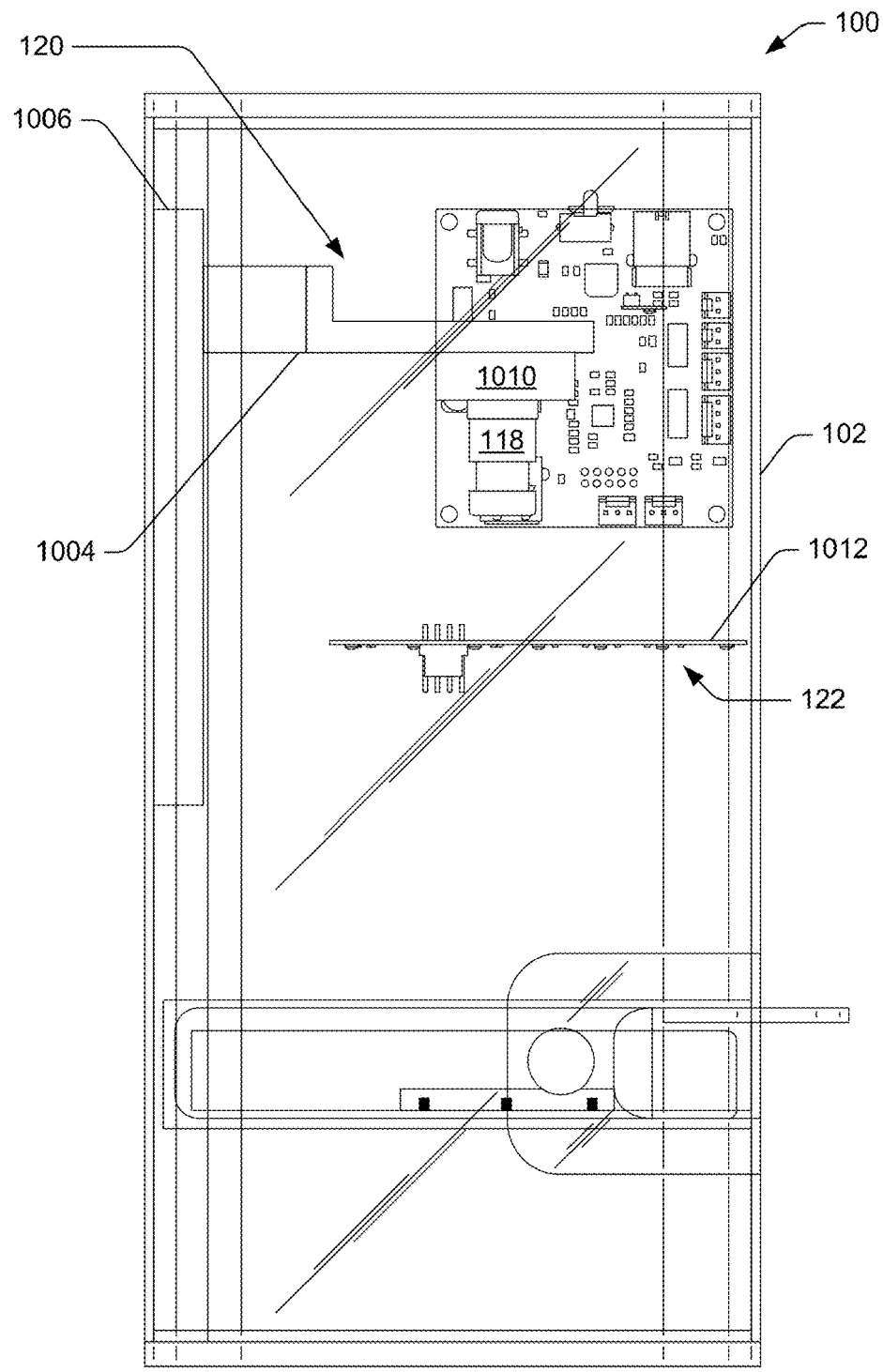
FIG. 11 is a side view of the substrate reader of FIG. 1, showing the example components housed within the substrate reader, according to an embodiment of the present disclosure.

FIG. 11 illustrates a side view of the substrate reader 100, showing the example components of the substrate reader 100 disposed within the housing 102. The housing 102 is shown as transparent to illustrate the example components of the substrate reader 100.

As discussed above, the positioning system 120 includes the mounts 1004, the track 1006, and the carrier 1010 for positioning the image capturing device 118 relative to the substrate test strip. For example, the image capturing device 118 may translate in the vertical direction (Y-direction) via the mounts 1004 engaging with the track 1006. As noted above, in an embodiment, motors or other actuators may be used to position the image capturing device 118 within the housing 102. For example, one or more actuators may couple to the mounts 1004 and engage with the track 1006 to dispose the image capturing device 118 at varying heights.

Figure 12:
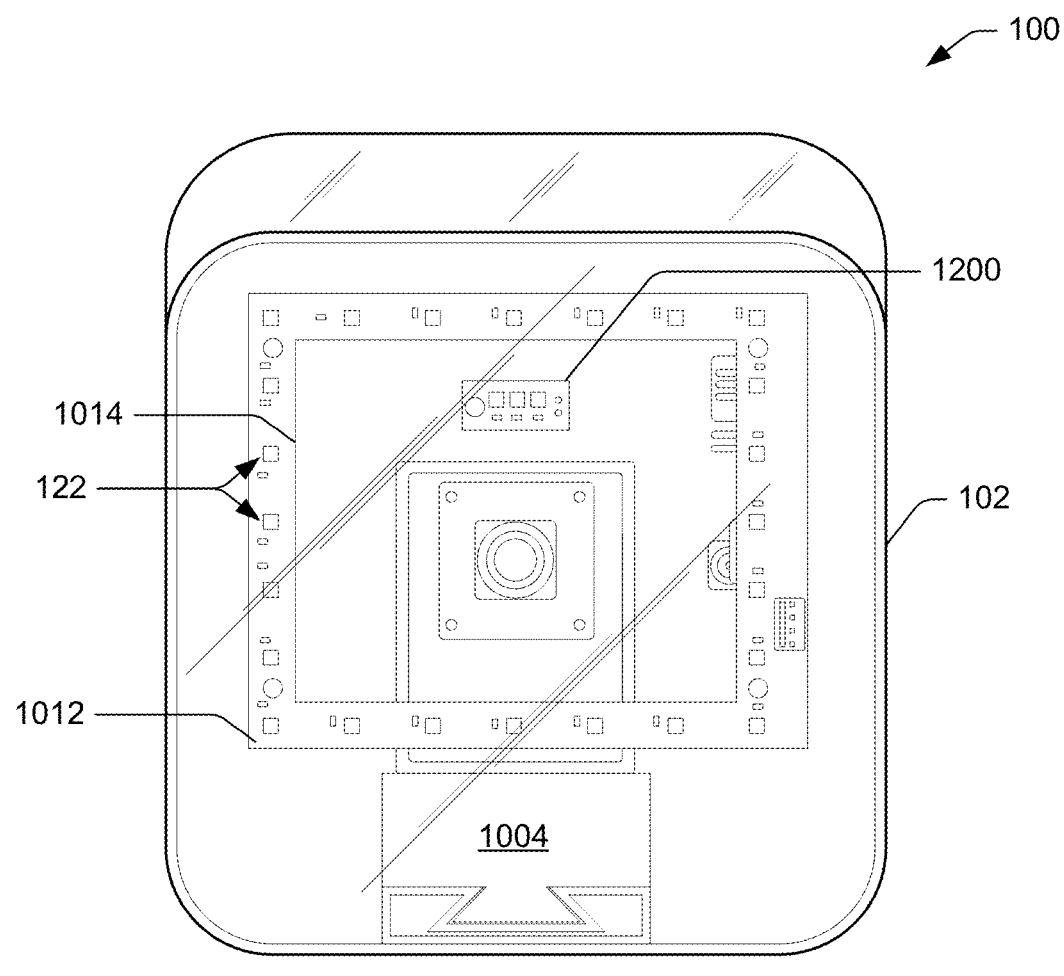
FIG. 12 is a bottom view the substrate reader of FIG. 1, showing the example components housed within the substrate reader, according to an embodiment of the present disclosure.

FIG. 12 illustrates a bottom view of the substrate reader 100, showing the example components of the substrate reader 100 disposed within the housing 102. The housing 102 is shown as transparent to illustrate the example components of the substrate reader 100. Additionally, in FIG. 12, the cabinet 110 and the slide 112 are removed from the housing 102 to more clearly illustrate the example components.

The lighting element(s) 122 are shown disposed on the PCB 1012. As shown in FIG. 10, the PCB 1012 may include a square-shaped PCB having the opening 1014 through which the image capturing device 118 captures images of the substrate test strip.

In an embodiment, the substrate reader 100 may also include additional lighting element(s) 1200. The additional lighting element(s) 1200 may be arranged to provide light for the image capturing device 118.

Figure 13:
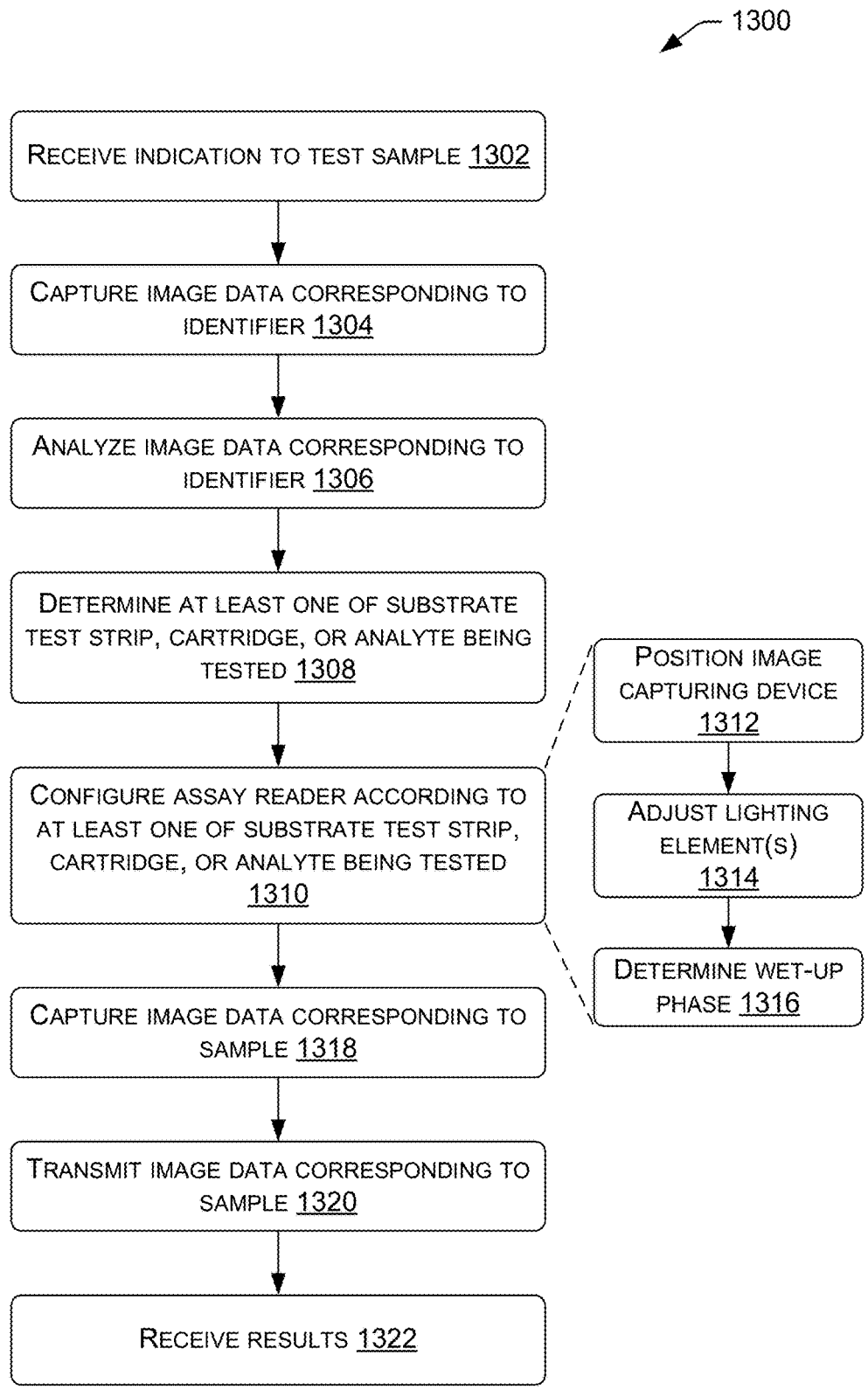
FIG. 13 is an example method implemented by the substrate reader of FIG. 1, according to an embodiment of the present disclosure.

FIG. 13 illustrates an exemplary process 1300 performed in accordance with aspects of the present invention for processing image data of a substrate test strip to generate qualitative, semi-quantitative, and/or quantitative data. The process 1300 described herein is illustrated as collections of blocks in logical flow diagrams, which represent a sequence of operations, some or all of which may be implemented in hardware, software, or a combination thereof. In the context of software, the blocks may represent computer-executable instructions stored on one or more computer readable media that, when executed by one or more processors, program the processors to perform the recited operations. Generally, computer-executable instructions include routines, programs, objects, components, data structures etc. that perform particular functions or implement particular data types. The order in which the blocks are described should not be construed as a limitation, unless specifically noted. Any number of the described blocks may be combined in any order and/or in parallel to implement the process, or alternative processes, and not all of the blocks need be executed. In an embodiment, the process 1300 may be performed at least in part by the substrate reader 100. Additionally, or alternatively, the process 1300 be implemented in a wide variety of other environments, architectures, and systems.

At 1302, the substrate reader 100 may receive an indication to test a sample. For example, the processor(s) 124 may receive an indication to test the sample. As an example, an operator of the substrate reader 100 may press a button to "power on" the substrate reader 100 and/or may press a button associated with testing the sample. In an embodiment, the processor(s) 124 may receive an indication to test the sample based on the slide 112 being closed. In some examples, based at least in part on receiving the indication to test the sample, the processor(s) 124 may transmit a signal or otherwise cause the locking assembly 148 to lock. In an embodiment, the locking assembly 148 may remain locked until the substrate test strip (or image data pertaining thereto) has been analyzed.

At 1304, the substrate reader 100 may capture image data corresponding to an identifier of the substrate test strip, the cartridge, and/or the analyte being tested. For example, based at least in part on the processor(s) 124 receiving an indication to test the sample, the processor(s) 124 may capture image data, via the image capturing device 118, corresponding to the identifier 912 of the cartridge 900.

At 1306, the substrate reader 100 may analyze the image data corresponding to the identifier 912. For example, the processor(s) 124 may receive the image data captured at 1304 and may analyze the image data corresponding to the identifier 912. Additionally, or alternatively, in an embodiment, the processor(s) 124 may transmit, via the network interface(s) 142, the image data corresponding to the identifier 912 to the remote computing resources 134.

At 1308, the substrate reader 100 may determine at least one of a substrate test strip, a cartridge, and/or an analyte being tested. For example, the processor(s) 124 may compare the image data corresponding to identifier 912 to information contained in one or more databases (e.g., the substrate test strip database 128, the cartridge database 130, and/or the analyte database 132) to determine the substrate test strip, the cartridge, and/or the analyte being tested. By way of example, the processor(s) 124 may determine the substrate test strip is a lateral flow assay test strip, the cartridge is a single well cartridge, and the analyte being tested is human chorionic gonadotropin (hCG). However, the processor(s) 124 may determine additional information based at least in part on the identifier 912, or stated alternatively, the identifier 912 may be associated with other information. For example, in analyzing the image data corresponding to the identifier 912, the processor(s) 124 may determine information associated with the patient (e.g., age, sex, medical history, etc.). In an embodiment, where the processor(s) 124 transmit the image data to the remote computing resources 134 for processing, the processor(s) 124 may receive, via the network interface(s) 142, information corresponding to the substrate test strip, the cartridge, and/or the analyte being tested.

At 1310, the substrate reader 100 may be configured according to the substrate test strip, the cartridge, and/or the analyte being tested. In an embodiment, based at least in part on the substrate test strip, the cartridge, and/or the analyte being tested, one or more components of the substrate reader 100 may adjust, adapt, or configure. For example, based at least in part on the substrate test strip, the cartridge, and/or the analyte being tested, the processor(s) 124 may cause and/or transmit control signals to components of the substrate reader 100 for configuring the substrate reader 100. As shown by the sub-blocks in FIG. 13, the process 1300 may involve more detailed operations for configuring the substrate reader 100. For example, configuring the substrate reader 100 may include sub-blocks 1312, 1314, and/or 1316.

At 1312, depending on at least one of the type of substrate test strip, the cartridge, and/or the analyte being tested, the processor(s) 124 may transmit a control signal that causes the image capturing device 118 to reposition to capture an exposed portion (e.g., the test region 906) of the substrate test strip. In other words, depending on the cartridge, for example, an exposed portion of substrate test strip for imaging may vary. In some examples, the processor(s) 124 may cause the image capturing device 118 to position or maneuver based on information contained in the substrate test strip database 128, the cartridge database 130, and/or the analyte database 132. In an embodiment, the processor(s) 124 may transmit a control signal to the positioning system 120 to maneuver the image capturing device 118 horizontally or vertically, relative to the substrate test strip, and/or to tilt the image capturing device 118 at a particular angle relative to the substrate test strip. That is, depending on the substrate test strip and/or the analyte being tested, the processor(s) 124 may cause the positioning system 120 to maneuver the image capturing device 118 to align with the substrate test strip and/or position the image capturing device 118 closer or farther away from the substrate test strip. Positioning the image capturing device 118 closer to the substrate test strip, for example, may increase a quality of images captured by the image capturing device 118, which may in turn increase a sensitivity of the substrate reader 100 or the remote computing resources 134 when analyzing the images.

At 1314, depending on at least one of the type of substrate test strip, the cartridge, and/or the analyte being tested, the processor(s) 124 may transmit a control signal to adjust one or more characteristics of the lighting element(s) 122. For example, the processor(s) 124 may increase or decrease a brightness of light emitted by the lighting element(s) 122, may adjust a color of light emitted by the lighting element(s) 122, may cause certain lights of the lighting element(s) 122 to turn on, may cause certain lights of the lighting element(s) 122 to turn off, may cause the lighting element(s) 122 to emit a particular wavelength range, and/or emit light with a particular polarization. For example, the lighting element(s) 122 may be selectively turned on/off to focus light on the test region 906 of the substrate test strip. Adjusting the characteristics of the lighting element(s) 122 may increase a quality of image data captured (e.g., reducing glare). For example, emitting blue light via the lighting element(s) 122 may permit the image capturing device 118 to capture higher quality of images for determining the presence (or absence) of certain analytes. In some examples, the processor(s) 124 may cause the lighting element(s) 122 to adjust using or according to information contained in the substrate test strip database 128, the cartridge database 130, and/or the analyte database 132.

At 1316, depending on at least one of the type of substrate test strip, the cartridge, and/or the analyte being tested, the processor(s) 124 may determine a wet-up phase. The wet-up phase may represent an amount of time before the substrate test strip may be analyzed or an amount of time the fluid sample takes to react with the reagent in the substrate test strip to produce a visual indicator. For example, after placing the fluid sample on the substrate test strip, the fluid may take time to traverse the substrate test strip (e.g., wick) or may take time to react with the reagent in the substrate test strip. In an embodiment, the amount of time before capturing images of the substrate test strip may depend on characteristics of the substrate test strip (e.g., material, reagent, size, etc.) and/or the analyte being tested (e.g., viscosity, concentration, etc.).

Moreover, in an embodiment, the substrate reader 100 may continuously monitor or image the substrate test strip to determine when the image capturing device 118 may capture images for analysis. For example, during the wet-up phase, the image capturing device 118 may capture images, and using these images, may determine whether the substrate test strip is ready for analysis through comparing the image data against reference images (e.g., kinetic analysis). In such embodiments, upon determining that the substrate test strip is ready for imaging, the processor(s) 124 may cause the image capturing device 118 to capture images.

At 1318, the substrate reader 100 may capture image data corresponding to the sample. For example, the processor(s) 124 may cause the image capturing device 118 to capture an image of the substrate test strip. In an embodiment, the image capturing device 118 may capture a single image or a series of images.

At 1320, the substrate reader 100 may transmit the image data corresponding to the sample. For example, upon capturing the image data, the processor(s) 124 may transmit, using the network interface(s) 142, the image data corresponding to the sample to the remote computing resources 134 for image processing to determine the presence (or absence) of the analyte. In an embodiment, the image processing performed by the remote computing resources 134 may provide qualitative, semi-quantitative, and/or quantitative results. For example, the remote computing resources 134 may compare the image data or an intensity captured within the image data with a reference standard to determine the presence or an amount of an analyte present in the fluid sample. In an embodiment, the remote computing resources 134 may analyze the image data to determine whether the image data contains coloring above a detection line that indicates the presence of an analyte. Although analysis of the image data is discussed as being performed by the remote computing resources 134, the analysis or a portion thereof may be performed locally on the substrate reader 100.

At 1322, the substrate reader 100 may receive results associated with the testing. For example, the processor(s) 124 may receive, via the network interface(s) 142, results from the remote computing resources 134. In an embodiment, the results may indicate that image processing has been performed on the image data. Additionally, or alternatively, the results may indicate a poor quality of image data and the remote computing resources 134 may request to capture additional image data. In an embodiment, based at least in part on receiving the results, the substrate reader 100 may output a visual or audible indication indicating a completion of testing the substrate test strip. For example, the processor(s) 124 may cause one or more light(s) to illuminate. Additionally, or alternatively, upon receiving the results, the processor(s) 124 may cause the locking assembly 148 to unlock such that substrate test strip may be removed.

While the foregoing invention is described with respect to the specific examples, it is to be understood that the scope of the invention is not limited to these specific examples. Since other modifications and changes varied to fit particular operating requirements and environments will be apparent to those skilled in the art, the invention is not considered limited to the example chosen for purposes of disclosure, and covers all changes and modifications which do not constitute departures from the true spirit and scope of this invention.

Although the application describes embodiments having specific structural features and/or methodological acts, it is to be understood that the claims are not necessarily limited to the specific features or acts described. Rather, the specific features and acts are merely illustrative an embodiment that fall within the scope of the claims of the application.

What is claimed is:

1. A system comprising:
a housing including a slide that transitions between an open state and a closed state, the slide configured to receive a cartridge having a substrate test strip;
a camera;
a positioning system operably coupled to the camera;
a light source configured to emit light on the substrate test strip;
one or more processors; and
one or more non-transitory computer-readable media storing computer-executable instructions that, when executed by the one or more processors, cause the one or more processors be configured to:
receive a request to capture an image of the substrate test strip,
receive, via the camera, first image data representing an identifier of the cartridge,
determine, based at least in part on the identifier, a type of substrate test strip,
position, via the positioning system, the camera relative to at least a portion the substrate test strip based at least in part on the type of substrate test strip,
illuminate the light source based at least in part on the type of substrate test strip,
cause the camera to capture second image data representing the at least the portion of the substrate test strip,
transmit the second image data to one or more computing resources for image processing, and
receive, from the one or more computing resources, an indication that image processing has been performed on the second image data.

2. The system of claim 1, wherein the light source includes a plurality of light sources arranged around the cartridge.

3. The system of claim 1, further comprising a light indicator configured to illuminate based, at least in part, on an operational state of the system,
wherein the one or more non-transitory computer-readable media store computer-executable instructions, when executed by the one or more processors, cause the one or more processors to further be configured to:
illuminate the light indicator according to a first appearance state based at least in part on receiving the request; and
illuminate the light indicator according to a second appearance state based at least in part on the camera capturing the second image data.

4. The system of claim 1, further comprising a locking assembly configured to unlock and lock the slide, wherein the one or more non-transitory computer-readable media store computer-executable instructions that, when executed by the one or more processors, cause the one or more processors to further be configured to:
lock, via the locking assembly, the slide based at least in part on receiving the request; and
unlock, via the locking assembly, the slide based at least in part on receiving the indication.

5. The system of claim 1, wherein the one or more non-transitory computer-readable media store computer-executable instructions that, when executed by the one or more processors, cause the one or more processors to further be configured to determine, based at least in part on the identifier, at least one of a type of cartridge holding the substrate test strip or an analyte being tested using the substrate test strip,
wherein positioning the camera is based at least in part on at least one of the type of cartridge or the analyte being tested, and
wherein illuminating the light source is based at least in part on at least one of the type of cartridge or the analyte being tested.

6. A device comprising:
one or more processors; and
one or more non-transitory computer-readable media storing computer-executable instructions that, when executed by the one or more processors, cause the one or more processors to be configured to:
receive a request to capture an image of a substrate test strip;
determine a type of substrate test strip associated with the substrate test strip;
based at least in part on the type of substrate test strip, at least one of:
position an image capturing device relative to the substrate test strip via one or more actuators, or
illuminate at least a portion of the substrate test strip via one or more light sources;
capture image data corresponding the substrate test strip;
send the image data to one or more computing resources for image processing; and
receive an indication representing a completion of the image processing.

7. The device of claim 6, wherein illuminating the at least the portion of the substrate test strip via the one or more light sources includes at least one of:
illuminating the one or more light sources to a predetermined brightness; or
illuminating the one or more light sources to a particular color.

8. The device of claim 6, wherein the one or more non-transitory computer-readable media store computer-executable instructions that, when executed by the one or more processors, cause the one or more processors to further be configured to:
determine a type of cartridge holding the substrate test strip; and
determine an analyte being tested using the substrate test strip,
wherein at least one of positioning an image capturing device or illuminating the at least the portion of the substrate test strip is based at least in part on at least one of the type of cartridge or the analyte being tested.

9. The device of claim 6, wherein the one or more actuators are configured to move the image capturing device at least one of vertically or horizontally relative to the substrate test strip.

10. The device of claim 6, wherein the one or more non-transitory computer-readable media store computer-executable instructions that, when executed by the one or more processors, cause the one or more processors to further be configured to:
illuminate a light indicator according to a first appearance state based at least in part on receiving the request;
illuminate the light indicator according to a second appearance state based at least in part on capturing the image data, the second appearance state being different than the first appearance state; and
illuminate the light indicator according to a third appearance state based at least in part on receiving the indication, the third appearance state being different than the second appearance state.

11. The device of claim 6, wherein the one or more non-transitory computer-readable media store computer-executable instructions that, when executed by the one or more processors, cause the one or more processors to further be configured to:
determine an analyte being tested with the substrate test strip; and
determine a time at which to capture the image data based at least in part on at least one of:
the substrate test strip, or
the analyte being tested.

12. A device comprising:
a housing;
a light source configured to emit light on a sample disposed within the housing, the light emitted based at least in part on at least one of an analyte being tested within the sample or a container holding the sample;
an image capturing device configured to capture image data associated with the sample; and
one or more actuators operably coupled to the image capturing device, the one or more actuators configured to position the image capturing device relative to the sample based at least in part on the at least one of the analyte being tested or the container holding the sample.

13. The device of claim 12, wherein:
the light source includes a plurality of light sources arranged around the sample; and
individual light sources of the plurality of light sources are configured to emit light independently onto the sample based at least in part on the sample.

14. The device of claim 13, wherein the plurality of light sources are disposed around the image capturing device.

15. The device of claim 12, wherein the light source is configured to at least one of emit light of a predetermined color or emit light of a predetermined brightness.

16. The device of claim 12, further comprising a slide to hold the sample, the slide being moveable between an open state and a closed state within the housing.

17. The device of claim 16, further comprising a locking assembly to lock the slide in the closed state and unlock the slide in the open state.

18. The device of claim 12, further comprising a slide to hold the sample, wherein the slide includes at least one of fins, receptacles, or protrusions arranged within the housing to hold the sample in a fixed position.

19. The device of claim 12, wherein the one or more actuators adjust a position of the image capturing device in at least one of a vertical direction or a horizontal direction, relative to the sample.

20. The device of claim 6, wherein the one or more non-transitory computer-readable media store computer-executable instructions that, when executed by the one or more processors, cause the one or more processors to further be configured to:
lock the device based at least in part on receiving the request; and
unlock the device based at least in part on receiving the indication.

* * * * *